US007611711B2

(12) United States Patent
Alitalo et al.

(10) Patent No.: US 7,611,711 B2
(45) Date of Patent: Nov. 3, 2009

(54) VEGFR-3 INHIBITOR MATERIALS AND METHODS

(75) Inventors: Kari Alitalo, University of Helsinki (FI); Erkki Koivunen, University of Helsinki (FI); Hajime Kubo, University of Helsinki (FI)

(73) Assignee: Vegenics Limited, Toorak, Victoria (AU)

( * ) Notice: Subject to any disclaimer, the term of this patent is extended or adjusted under 35 U.S.C. 154(b) by 57 days.

(21) Appl. No.: 10/046,922

(22) Filed: Jan. 15, 2002

(65) Prior Publication Data

US 2002/0164667 A1 Nov. 7, 2002

Related U.S. Application Data

(60) Provisional application No. 60/262,476, filed on Jan. 17, 2001.

(51) Int. Cl.

| | |
|---|---|
| ***A61K 38/10*** | (2006.01) |
| ***A61K 38/12*** | (2006.01) |
| ***A61K 38/16*** | (2006.01) |
| ***A61K 39/44*** | (2006.01) |
| ***A61K 51/08*** | (2006.01) |
| ***C07K 11/00*** | (2006.01) |
| ***C07K 5/12*** | (2006.01) |
| ***C07K 1/13*** | (2006.01) |
| ***C07K 9/00*** | (2006.01) |
| ***C07K 7/02*** | (2006.01) |

(52) U.S. Cl. .................... 424/185.1; 530/329; 530/328; 530/327; 530/326; 530/325; 530/324; 530/317; 530/323; 530/391.1; 530/391.7; 424/1.57; 424/1.69; 424/192.1; 424/193.1; 514/11; 514/19

(58) Field of Classification Search ................. 530/328, 530/350; 424/185, 192.1, 185.1
See application file for complete search history.

(56) References Cited

U.S. PATENT DOCUMENTS

| | | | | |
|---|---|---|---|---|
| 4,975,278 | A * | 12/1990 | Senter et al. | 424/178.1 |
| 5,607,918 | A | 3/1997 | Eriksson et al. | 514/12 |
| 5,776,755 | A | 7/1998 | Alitalo et al. | 435/194 |
| 5,840,693 | A | 11/1998 | Eriksson et al. | 514/12 |
| 5,932,540 | A | 8/1999 | Hu et al. | 514/2 |
| 5,935,820 | A | 8/1999 | Hu et al. | 435/69.4 |
| 5,952,199 | A | 9/1999 | Davis-Smyth | 435/69.7 |
| 6,040,157 | A | 3/2000 | Hu et al. | 435/69.4 |
| 6,100,071 | A | 8/2000 | Davis-Smyth | 435/69.7 |
| 6,107,046 | A | 8/2000 | Alitalo et al. | 435/7.1 |
| 6,121,416 | A * | 9/2000 | Clark et al. | 530/326 |
| 6,130,071 | A | 10/2000 | Alitalo et al. | 435/69.4 |
| 6,221,839 | B1 | 4/2001 | Alitalo et al. | 512/12 |
| 6,235,713 | B1 | 5/2001 | Achen et al. | 514/12 |
| 6,245,530 | B1 | 6/2001 | Alitalo et al. | |
| 6,331,302 | B1 | 12/2001 | Bennett | 424/146.1 |
| 6,361,946 | B1 | 3/2002 | Alitalo et al. | 435/6 |
| 6,383,484 | B1 | 5/2002 | Achen et al. | 424/133.1 |
| 6,383,486 | B1 | 5/2002 | Davis-Smyth | 424/158.1 |
| 6,403,088 | B1 | 6/2002 | Alitalo | 424/139.1 |
| 6,451,764 | B1 | 9/2002 | Lee et al. | 514/12 |
| 6,576,608 | B1 | 6/2003 | Lee et al. | 514/2 |
| 6,608,182 | B1 | 8/2003 | Rosen et al. | 530/399 |
| 6,645,933 | B1 | 11/2003 | Alitalo et al. | 514/2 |
| 6,673,343 | B2 | 1/2004 | Bennett et al. | 424/133.1 |
| 6,689,580 | B1 | 2/2004 | Achen et al. | 435/69.1 |
| 6,730,489 | B1 | 5/2004 | Achen et al. | 435/7.1 |
| 6,730,658 | B1 | 5/2004 | Alitalo et al. | 514/12 |
| 2001/0038842 | A1 | 11/2001 | Achen et al. | |
| 2002/0048763 | A1 * | 4/2002 | Penn et al. | 435/6 |
| 2002/0065218 | A1 | 5/2002 | Achen et al. | |
| 2002/0102260 | A1 | 8/2002 | Achen et al. | |
| 2002/0120123 | A1 | 8/2002 | Rosen et al. | |
| 2002/0123481 | A1 | 9/2002 | Oliviero | |
| 2002/0127222 | A1 | 9/2002 | Achen et al. | |
| 2002/0146420 | A1 | 10/2002 | Bennett et al. | |
| 2002/0151489 | A1 | 10/2002 | Gravereaux et al. | |
| 2002/0182683 | A1 | 12/2002 | Hu et al. | |
| 2002/0197691 | A1 | 12/2002 | Sugiyama | |
| 2003/0008357 | A1 | 1/2003 | Hu et al. | |
| 2003/0028007 | A1 | 2/2003 | Hu et al. | |
| 2003/0091567 | A1 | 5/2003 | Alitalo et al. | |
| 2003/0092604 | A1 | 5/2003 | Davis-Smyth et al. | |

(Continued)

FOREIGN PATENT DOCUMENTS

| | | |
|---|---|---|
| EP | 0935001 | 8/1999 |

(Continued)

OTHER PUBLICATIONS

Lee et al, Proc Nat. Acad. Sci USA 93: 1988-1992, Mar. 1996.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Curnis et al, Nat Biotechnol 18(11): 1185-90, Nov. 2000.*
Hirohashi et al, Mol Pharmacol 53(6): 1068-75, Jun. 1998.*
Attwood et al, The Babel of Bioinformatics, 2000, Science vol. 290 No. 5491: 471-473.*
Baldwin et al, J Biol Chem 276(22): 19166-19171, 2001.*
Mason et al, Molecular Endocrinology 8(3): 325-332, 1994.*
Yamada et al, Blood 97(6): 1671-1678, Mar. 2001.*

(Continued)

*Primary Examiner*—Phuong Huynh
(74) *Attorney, Agent, or Firm*—Marshall, Gerstein & Borun LLP

(57) ABSTRACT

The present invention relates to the diagnosis, evaluation, and therapeutic intervention of disorders mediated by the activity of cell surface receptor VEGFR-3, which activity often is stimulated by VEGFR-3 ligands VEGF-C and VEGF-D. More particularly, the present invention identifies novel methods and compositions for the inhibition of VEGF-C/D binding to VEGFR-3. The compositions of the present invention will be useful in the inhibition of angiogenesis and lymphangiogenesis.

23 Claims, 1 Drawing Sheet

U.S. PATENT DOCUMENTS

| | | | |
|---|---|---|---|
| 2003/0125537 A1 | 7/2003 | Achen et al. |
| 2003/0166523 A1 | 9/2003 | Achen et al. |
| 2003/0166547 A1 | 9/2003 | Oliviero |
| 2003/0166873 A1 | 9/2003 | Lee et al. |
| 2003/0170786 A1 | 9/2003 | Rosen et al. |
| 2003/0175274 A1 | 9/2003 | Rosen et al. |
| 2003/0176674 A1 | 9/2003 | Rosen et al. |
| 2003/0180294 A1 | 9/2003 | DeVries |
| 2003/0211101 A1 | 11/2003 | Wise et al. |
| 2003/0211988 A1 | 11/2003 | Epstein |
| 2003/0215921 A1 | 11/2003 | Coleman |
| 2003/0228283 A1 | 12/2003 | Heinzerling et al. |
| 2003/0232437 A1 | 12/2003 | Zhang et al. |
| 2004/0037820 A1 | 2/2004 | Alitalo et al. |

FOREIGN PATENT DOCUMENTS

| | | |
|---|---|---|
| WO | WO 96/26736 | 9/1996 |
| WO | WO 97/12972 | 4/1997 |
| WO | WO 98/02543 | 1/1998 |
| WO | WO 98/07832 | 2/1998 |
| WO | WO 98/33917 | 8/1998 |
| WO | WO 99/25869 | 5/1999 |
| WO | WO 99/30157 | 6/1999 |
| WO | WO 99/40947 | 8/1999 |
| WO | WO 99/60025 | 11/1999 |
| WO | WO 00/21560 | 4/2000 |
| WO | WO 00/45835 | 8/2000 |
| WO | WO 00/52054 | 9/2000 |
| WO | WO 00/62063 | 10/2000 |
| WO | WO 01/52875 | 7/2001 |
| WO | WO 2004/009773 | 1/2004 |

OTHER PUBLICATIONS

Dermer et al, Bio/Technology 12; 320, 1994.*
Gura et al, Science 278: 1041-1042, 1997.*
Achen, et al., *Proc. Nat'l. Acad. Sci. USA*, 95:548-553 (1998).
Achen, et al., *Eur. J. Biochem.*, 267(9):2505-2515 (2000).
Aprelikova, et al., *Cancer Res.*, 52:746-748 (1992).
Banerji, et al., *J. Cell Biol.*, 144:789-801 (1999).
Bellomo, et al., *Circ. Res.*, E-29-E35 (2000).
Breier, et al., *Dev.*, 114:521-532 (1992).
Cao et al., *J. Biol. Chem.*, 271:3154-3162 (1996).
Dumont, et al., *Science*, 282:946-949 (1998).
Ferrara, *J. Mol. Med.*, 77:527-543 (1999).
Ferrara and Alitalo, *Nature Med.*, 5:1359-1364 (1999).
Fidler, et al., *Adv. Cancer Res.*, 28:149-250 (1978).
Folkman, et al., *Proc. Nat'l. Acad. Sci. USA*, 76:5217-5221 (1979).
Fraley, et al., *Proc. Nat'l. Acad. Sci. USA*, 76:3348-3352 (1979).
GenBank Accession No. AF106020.
GenBank Accession No. NM_003872.
GenBank Accession No. NM_003873.
GenBank Accession No. NM_005429.
GenBank Accession No. P15692.
GenBank Accession No. S67520.
GenBank Accession No. S67522.
GenBank Accession No. U48801.
GenBank Acession No. XM_003852.
GenBank Accession No. X06374.
GenBank Accession No. X54936.
GenBank Accession No. X61656.
GenBank Accession No. X94216.
Koivunen, et al., *Methods Mol. Biol.*, 129:3-17 (1999).
Koivunen, et al., *Biotechnol.*, 18(8):768-74 (1999).
Liotta, et al., *Cancer Treatment Res.*, 40:223-238 (1988).
Maglione, et al., *Oncogene*, 8:925-931 (1993).
Mandriota, et al., *The EMBO Journal*, 20:672-682 (2001).
Matthews, et al., *Proc. Nat'l. Acad. Sci. USA*, 88:9026-9030 (1991).
Meyer, et al., *The EMBO J.*, 18:363-374 (1999).
Miles and Miles, *J. Physiol.*, 118:228-257 (1952).
Muller, et al., *Structure*, 5:1325-1338 (1997).
Muragaki, et al., *Proc. Nat'l. Acad. Sci.* (USA), 92:8763-8767 (1995).
National Institutes of Health http://cancertrials.nci.nih.gov/news/angio.
Nelson, et al., *J. Cell Biol.*, 97:244-251 (1983).
Neufeld, et al., *The FASEB J.*, 13:9-22 (1999).
Nicolson, *Biochim. Biophy. Acta*, 948:175-224 (1988).
Oh, et al., *Dev. Biol.*, 188:96-109 (1997).
Ortega, et al., *Fron. Biosci.*, 4:141-152 (1999).
Pajusola, et al., *Oncogene*, 9:3545-3555 (1994).
Pertovaara, et al., *J. Biol. Chem.*, 269:6271-6274 (1994).
Petrova, et al., *Exp. Cell Res.*, 253:117-130 (1999).
Risau, et al., *Dev. Biol.*, 125:441-450 (1988).
Rivera-Baeza, et al., *Neuropeptides*, 30:327-333 (1996).
Rosenkranz, et al., *Growth Factors*, 16:201-216 (1999).
Schmelz, et al., *Differentiation*, 57:97-117 (1994).
Skobe, et al., *Nature Medicine*, 7:192-198 (2001).
Smith and Scott, *Methods Enzymol.*, 217:228-257 (1993).
Stacker and Achen, *Growth Factors*, 17:1-11 (1999).
Stacker, et al., *Nature Medicine*, 7:186-191 (2001).
Taipale, et al., *Curr. Top. Microbiol. Immunol.*, 237:85-96 (1999).
Terman, et al., *Biochem. Biophys. Res. Comm.*, 187:1579-1586 (1992).
Valtola, et al., *Am. J. Pathol.*, 154:1381-1390 (1999).
Vassar, et al., *Proc. Nat'l. Acad. Sci. USA*, 86:1563-1567 (1989).
Vassar and Fuchs, *Genes Dev.*, 5:714-727 (1991).
Waltenberger, et al., *The J. Biol. Chem.*, 269:26988-26995 (1994).
Zachary, *The Intl. J. Biochem. Cell Biol.*, 30:1169-1174 (1998).
Zetter, *N. Eng. J. Med.*, 322:605-612 (1990).

* cited by examiner

SEQUENCE LISTING

```
<160> NUMBER OF SEQ ID NOS: 80

<210> SEQ ID NO 1
<211> LENGTH: 13
<212> TYPE: PRT
<213> ORGANISM: conserved PDGF motif
<220> FEATURE:
<221> NAME/KEY: SITE
<222> LOCATION: (2)..(2)
<223> OTHER INFORMATION: X= proline or serine
<221> NAME/KEY: SITE
<222> LOCATION: (10)..(10)
<223> OTHER INFORMATION: X= glycine or serine or threonine or alanine
<221> NAME/KEY: SITE
<222> LOCATION: (5)..(7)
<223> OTHER INFORMATION: X= any amino acid

<400> SEQUENCE: 1

Pro Xaa Cys Val Xaa Xaa Xaa Arg Cys Xaa Gly Cys Cys
1               5                   10


<210> SEQ ID NO 2
<211> LENGTH: 76
<212> TYPE: PRT
<213> ORGANISM: VEGF homology domain
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine, or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
```

-continued

```
<223> OTHER INFORMATION: X is glycine, serine, threonine, or alanine
<221> NAME/KEY: SITE
<222> LOCATION: (37)..(42)
<223> OTHER INFORMATION: X is any amino acid
<221> NAME/KEY: SITE
<222> LOCATION: (44)..(75)
<223> OTHER INFORMATION: X is any amino acid

<400> SEQUENCE: 2

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Cys
65                  70                  75


<210> SEQ ID NO 3
<211> LENGTH: 77
<212> TYPE: PRT
<213> ORGANISM: VEGF homology domain (VHD)
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine, or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine, or alanine
<221> NAME/KEY: SITE
<222> LOCATION: (37)..(42)
<223> OTHER INFORMATION: X is any amino acid
<221> NAME/KEY: SITE
<222> LOCATION: (44)..(76)
<223> OTHER INFORMATION: X is any amino acid

<400> SEQUENCE: 3

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Cys
65                  70                  75


<210> SEQ ID NO 4
<211> LENGTH: 78
<212> TYPE: PRT
<213> ORGANISM: VEGF homology domain (VHD)
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
```

-continued

```
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine, or alanine
<221> NAME/KEY: SITE
<222> LOCATION: (37)..(42)
<223> OTHER INFORMATION: X is any amino acid
<221> NAME/KEY: SITE
<222> LOCATION: (44)..(77)
<223> OTHER INFORMATION: X is any amino acid

<400> SEQUENCE: 4

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Cys
65                  70                  75


<210> SEQ ID NO 5
<211> LENGTH: 79
<212> TYPE: PRT
<213> ORGANISM: VEGF homology domain (VHD)
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(78)
<223> OTHER INFORMATION: X is any amino acid

<400> SEQUENCE: 5

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Cys
65                  70                  75


<210> SEQ ID NO 6
<211> LENGTH: 80
<212> TYPE: PRT
<213> ORGANISM: VEGF homology domain (VHD)
<220> FEATURE:
<221> NAME/KEY: SITE
```

-continued

<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine, or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(79)
<223> OTHER INFORMATION: X is any amino acid

<400> SEQUENCE: 6

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Cys
65                  70                  75                  80
```

<210> SEQ ID NO 7
<211> LENGTH: 81
<212> TYPE: PRT
<213> ORGANISM: VEGF homology domain (VHD)
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(80)
<223> OTHER INFORMATION: X is any amino acid

<400> SEQUENCE: 7

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Cys
```

-continued

<210> SEQ ID NO 8
<211> LENGTH: 82
<212> TYPE: PRT
<213> ORGANISM: VEGF homology domain (VHD)
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(81)
<223> OTHER INFORMATION: X is any amino acid

<400> SEQUENCE: 8

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Cys
```

<210> SEQ ID NO 9
<211> LENGTH: 83
<212> TYPE: PRT
<213> ORGANISM: VEGF homology domain
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(82)
<223> OTHER INFORMATION: X is any amino acid

<400> SEQUENCE: 9

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45
```

-continued

```
Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Cys


<210> SEQ ID NO 10
<211> LENGTH: 84
<212> TYPE: PRT
<213> ORGANISM: VEGF homology domain
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(83)
<223> OTHER INFORMATION: X is any amino acid

<400> SEQUENCE: 10

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Cys


<210> SEQ ID NO 11
<211> LENGTH: 85
<212> TYPE: PRT
<213> ORGANISM: VEGF homology domain
<220> FEATURE:
<221> NAME/KEY: SITE
<222> LOCATION: (2)..(23)
<223> OTHER INFORMATION: X is any amino acid
<221> NAME/KEY: SITE
<222> LOCATION: (25)..(25)
<223> OTHER INFORMATION: X is proline, serine or arginine
<221> NAME/KEY: SITE
<222> LOCATION: (28)..(30)
<223> OTHER INFORMATION: X is any amino acid
<221> NAME/KEY: SITE
<222> LOCATION: (33)..(33)
<223> OTHER INFORMATION: X is glycine, serine, threonine or alanine
<221> NAME/KEY: SITE
<222> LOCATION: (37)..(42)
<223> OTHER INFORMATION: X is any amino acid
<221> NAME/KEY: SITE
<222> LOCATION: (44)..(84)
<223> OTHER INFORMATION: X is any amino acid

<400> SEQUENCE: 11
```

-continued

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Xaa Cys Val Xaa Xaa Xaa Arg Cys
            20                  25                  30

Xaa Gly Cys Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Cys
                 85


<210> SEQ ID NO 12
<211> LENGTH: 77
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(76)
<223> OTHER INFORMATION: X is any amino acid

<400> SEQUENCE: 12

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Cys
65                  70                  75


<210> SEQ ID NO 13
<211> LENGTH: 78
<212> TYPE: PRT
<213> ORGANISM: VEGF homology domain (VHD)
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
```

-continued

```
<222> LOCATION: (38)..(43)
<223> OTHER INFORMATION: X is any amino acid
<221> NAME/KEY: SITE
<222> LOCATION: (45)..(77)
<223> OTHER INFORMATION: X is any amino acid

<400> SEQUENCE: 13

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Cys
65                  70                  75


<210> SEQ ID NO 14
<211> LENGTH: 79
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(78)
<223> OTHER INFORMATION: X is any amino acid

<400> SEQUENCE: 14

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Cys
65                  70                  75


<210> SEQ ID NO 15
<211> LENGTH: 80
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
```

-continued

<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(79)
<223> OTHER INFORMATION: X is any amino acid

<400> SEQUENCE: 15

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Cys
65                  70                  75                  80
```

<210> SEQ ID NO 16
<211> LENGTH: 81
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(80)
<223> OTHER INFORMATION: X is any amino acid

<400> SEQUENCE: 16

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Cys
```

<210> SEQ ID NO 17
<211> LENGTH: 82
<212> TYPE: PRT
<213> ORGANISM: VEGF homology domain
<220> FEATURE:
<221> NAME/KEY: SITE -continued
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(81)
<223> OTHER INFORMATION: X is any amino acid

<400> SEQUENCE: 17

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Cys
```

<210> SEQ ID NO 18
<211> LENGTH: 83
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(82)
<223> OTHER INFORMATION: X is any amino acid

<400> SEQUENCE: 18

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

-continued

```
Xaa Xaa Cys


<210> SEQ ID NO 19
<211> LENGTH: 84
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(83)
<223> OTHER INFORMATION: X is any amino acid

<400> SEQUENCE: 19

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Cys


<210> SEQ ID NO 20
<211> LENGTH: 85
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(84)
<223> OTHER INFORMATION: X is any amino acid

<400> SEQUENCE: 20

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30
```

-continued

```
Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Cys
                85


<210> SEQ ID NO 21
<211> LENGTH: 86
<212> TYPE: PRT
<213> ORGANISM: VEGF homology domain
<220> FEATURE:
<221> NAME/KEY: SITE
<222> LOCATION: (2)..(24)
<223> OTHER INFORMATION: X is any amino acid
<221> NAME/KEY: SITE
<222> LOCATION: (26)..(26)
<223> OTHER INFORMATION: X is proline, serine or arginine
<221> NAME/KEY: SITE
<222> LOCATION: (29)..(31)
<223> OTHER INFORMATION: X is any amino acid
<221> NAME/KEY: SITE
<222> LOCATION: (34)..(34)
<223> OTHER INFORMATION: X is glycine, serine, threonine or alanine
<221> NAME/KEY: SITE
<222> LOCATION: (38)..(43)
<223> OTHER INFORMATION: X is any amino acid
<221> NAME/KEY: SITE
<222> LOCATION: (45)..(85)
<223> OTHER INFORMATION: X is any amino acid

<400> SEQUENCE: 21

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa Arg
            20                  25                  30

Cys Xaa Gly Cys Cys Xaa Xaa Xaa Xaa Xaa Xaa Cys Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Cys
                    85


<210> SEQ ID NO 22
<211> LENGTH: 78
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
```

-continued

<222> LOCATION: (46)..(77)
<223> OTHER INFORMATION: X is any amino acid

<400> SEQUENCE: 22

Cys Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Pro Xaa Cys Val Xaa Xaa Xaa
20 25 30

Arg Cys Xaa Gly Cys Cys Xaa Xaa Xaa Xaa Xaa Xaa Cys Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Cys
65 70 75

<210> SEQ ID NO 23
<211> LENGTH: 79
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(78)
<223> OTHER INFORMATION: X is any amino acid

<400> SEQUENCE: 23

Cys Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Pro Xaa Cys Val Xaa Xaa Xaa
20 25 30

Arg Cys Xaa Gly Cys Cys Xaa Xaa Xaa Xaa Xaa Xaa Cys Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Cys
65 70 75

<210> SEQ ID NO 24
<211> LENGTH: 80
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)

-continued

<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(79)
<223> OTHER INFORMATION: X is any amino acid

<400> SEQUENCE: 24

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Cys
65                  70                  75                  80
```

<210> SEQ ID NO 25
<211> LENGTH: 81
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(80)
<223> OTHER INFORMATION: X is any amino acid

<400> SEQUENCE: 25

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Cys
```

<210> SEQ ID NO 26
<211> LENGTH: 82
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE -continued
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(81)
<223> OTHER INFORMATION: X is any amino acid

<400> SEQUENCE: 26

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Cys
```

<210> SEQ ID NO 27
<211> LENGTH: 83
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(82)
<223> OTHER INFORMATION: X is any amino acid

<400> SEQUENCE: 27

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Cys
```

-continued

<210> SEQ ID NO 28
<211> LENGTH: 84
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(83)
<223> OTHER INFORMATION: X is any amino acid

<400> SEQUENCE: 28

Cys Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Pro Xaa Cys Val Xaa Xaa Xaa
20 25 30

Arg Cys Xaa Gly Cys Cys Xaa Xaa Xaa Xaa Xaa Xaa Cys Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Cys

<210> SEQ ID NO 29
<211> LENGTH: 85
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(84)
<223> OTHER INFORMATION: X is any amino acid

<400> SEQUENCE: 29

Cys Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Pro Xaa Cys Val Xaa Xaa Xaa
20 25 30

Arg Cys Xaa Gly Cys Cys Xaa Xaa Xaa Xaa Xaa Xaa Cys Xaa Xaa Xaa
35 40 45

-continued

```
Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Cys
                85


<210> SEQ ID NO 30
<211> LENGTH: 86
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(85)
<223> OTHER INFORMATION: X is any amino acid

<400> SEQUENCE: 30

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Cys
                 85


<210> SEQ ID NO 31
<211> LENGTH: 87
<212> TYPE: PRT
<213> ORGANISM: VEGF homology domain
<220> FEATURE:
<221> NAME/KEY: SITE
<222> LOCATION: (2)..(25)
<223> OTHER INFORMATION: X is any amino acid
<221> NAME/KEY: SITE
<222> LOCATION: (27)..(27)
<223> OTHER INFORMATION: X is proline, serine or arginine
<221> NAME/KEY: SITE
<222> LOCATION: (30)..(32)
<223> OTHER INFORMATION: X is any amino acid
<221> NAME/KEY: SITE
<222> LOCATION: (35)..(35)
<223> OTHER INFORMATION: X is glycine, serine, threonine or alanine
<221> NAME/KEY: SITE
<222> LOCATION: (39)..(44)
<223> OTHER INFORMATION: X is any amino acid
<221> NAME/KEY: SITE
<222> LOCATION: (46)..(86)
<223> OTHER INFORMATION: X is any amino acid
```

-continued

<400> SEQUENCE: 31

```
Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Cys
                85
```

<210> SEQ ID NO 32
<211> LENGTH: 8
<212> TYPE: PRT
<213> ORGANISM: isolated polypeptide
<220> FEATURE:
<221> NAME/KEY: SITE
<222> LOCATION: (1)..(1)
<223> OTHER INFORMATION: X is glycine or a conservative substitution
<221> NAME/KEY: SITE
<222> LOCATION: (2)..(2)
<223> OTHER INFORMATION: X is tyrosine or a conservative substitution
<221> NAME/KEY: SITE
<222> LOCATION: (3)..(3)
<223> OTHER INFORMATION: X is tryptophan or a conservative substitution
<221> NAME/KEY: SITE
<222> LOCATION: (4)..(4)
<223> OTHER INFORMATION: X is leucine or a conservative substitution
<221> NAME/KEY: SITE
<222> LOCATION: (5)..(5)
<223> OTHER INFORMATION: X is threonine or a conservative substitution
<221> NAME/KEY: SITE
<222> LOCATION: (6)..(6)
<223> OTHER INFORMATION: X is isoleucine or a conservative substitution
<221> NAME/KEY: SITE
<222> LOCATION: (7)..(7)
<223> OTHER INFORMATION: X is tryptophan or a conservative substitution
<221> NAME/KEY: SITE
<222> LOCATION: (8)..(8)
<223> OTHER INFORMATION: X is glycine or a conservative substitution

<400> SEQUENCE: 32

```
Xaa Xaa Xaa Xaa Xaa Xaa Xaa Xaa
1               5
```

<210> SEQ ID NO 33
<211> LENGTH: 10
<212> TYPE: PRT
<213> ORGANISM: isolated peptide
<220> FEATURE:
<221> NAME/KEY: SITE
<222> LOCATION: (2)..(2)
<223> OTHER INFORMATION: X is glycine or a conservative substitution
<221> NAME/KEY: SITE
<222> LOCATION: (3)..(3)
<223> OTHER INFORMATION: X is tyrosine or a conservative substitution
<221> NAME/KEY: SITE
<222> LOCATION: (4)..(4)
<223> OTHER INFORMATION: X is tryptophan or a conservative substitution
<221> NAME/KEY: SITE
<222> LOCATION: (5)..(5)
<223> OTHER INFORMATION: X is leucine or a conservative substitution
<221> NAME/KEY: SITE
<222> LOCATION: (6)..(6)
<223> OTHER INFORMATION: X is threonine or a conservative substitution
<221> NAME/KEY: SITE
<222> LOCATION: (7)..(7)

-continued

<223> OTHER INFORMATION: X is isoleucine or a conservative substitution
<221> NAME/KEY: SITE
<222> LOCATION: (8)..(8)
<223> OTHER INFORMATION: X is tryptophan or a conservative substitution
<221> NAME/KEY: SITE
<222> LOCATION: (9)..(9)
<223> OTHER INFORMATION: X is glycine or a conservative substitution

<400> SEQUENCE: 33

Cys Xaa Xaa Xaa Xaa Xaa Xaa Xaa Xaa Cys
1 5 10

<210> SEQ ID NO 34
<211> LENGTH: 10
<212> TYPE: PRT
<213> ORGANISM: isolated peptide
<220> FEATURE:
<221> NAME/KEY: SITE
<222> LOCATION: (1)..(1)
<223> OTHER INFORMATION: X is any amino acid
<221> NAME/KEY: SITE
<222> LOCATION: (10)..(10)
<223> OTHER INFORMATION: X is any amino acid

<400> SEQUENCE: 34

Xaa Gly Tyr Trp Leu Thr Ile Trp Gly Xaa
1 5 10

<210> SEQ ID NO 35
<211> LENGTH: 10
<212> TYPE: PRT
<213> ORGANISM: isolated peptide

<400> SEQUENCE: 35

Cys Gly Tyr Trp Leu Thr Ile Trp Gly Cys
1 5 10

<210> SEQ ID NO 36
<211> LENGTH: 9
<212> TYPE: PRT
<213> ORGANISM: peptide

<400> SEQUENCE: 36

Ser Gly Tyr Trp Trp Asp Thr Trp Phe
1 5

<210> SEQ ID NO 37
<211> LENGTH: 9
<212> TYPE: PRT
<213> ORGANISM: peptide

<400> SEQUENCE: 37

Ser Cys Tyr Trp Arg Asp Thr Trp Phe
1 5

<210> SEQ ID NO 38
<211> LENGTH: 9
<212> TYPE: PRT
<213> ORGANISM: peptide

<400> SEQUENCE: 38

Lys Val Gly Trp Ser Ser Pro Asp Trp
1 5

<210> SEQ ID NO 39
<211> LENGTH: 9
<212> TYPE: PRT

-continued

<213> ORGANISM: peptide

<400> SEQUENCE: 39

Phe Val Gly Trp Thr Lys Val Leu Gly
1 5

<210> SEQ ID NO 40
<211> LENGTH: 9
<212> TYPE: PRT
<213> ORGANISM: peptide

<400> SEQUENCE: 40

Tyr Ser Ser Ser Met Arg Trp Arg His
1 5

<210> SEQ ID NO 41
<211> LENGTH: 9
<212> TYPE: PRT
<213> ORGANISM: peptide

<400> SEQUENCE: 41

Arg Trp Arg Gly Asn Ala Tyr Pro Gly
1 5

<210> SEQ ID NO 42
<211> LENGTH: 9
<212> TYPE: PRT
<213> ORGANISM: peptide

<400> SEQUENCE: 42

Ser Ala Val Phe Arg Gly Arg Trp Leu
1 5

<210> SEQ ID NO 43
<211> LENGTH: 9
<212> TYPE: PRT
<213> ORGANISM: peptide

<400> SEQUENCE: 43

Trp Phe Ser Ala Ser Leu Arg Phe Arg
1 5

<210> SEQ ID NO 44
<211> LENGTH: 8
<212> TYPE: PRT
<213> ORGANISM: peptide

<400> SEQUENCE: 44

Trp Gln Leu Gly Arg Asn Trp Ile
1 5

<210> SEQ ID NO 45
<211> LENGTH: 8
<212> TYPE: PRT
<213> ORGANISM: peptide

<400> SEQUENCE: 45

Val Glu Val Gln Ile Thr Gln Glu
1 5

<210> SEQ ID NO 46
<211> LENGTH: 8
<212> TYPE: PRT
<213> ORGANISM: peptide

-continued

<400> SEQUENCE: 46

Ala Gly Lys Ala Ser Ser Leu Trp
1 5

<210> SEQ ID NO 47
<211> LENGTH: 8
<212> TYPE: PRT
<213> ORGANISM: peptide

<400> SEQUENCE: 47

Arg Ala Leu Asp Ser Ala Leu Ala
1 5

<210> SEQ ID NO 48
<211> LENGTH: 7
<212> TYPE: PRT
<213> ORGANISM: peptide

<400> SEQUENCE: 48

Tyr Gly Phe Glu Ala Ala Trp
1 5

<210> SEQ ID NO 49
<211> LENGTH: 7
<212> TYPE: PRT
<213> ORGANISM: peptide

<400> SEQUENCE: 49

Tyr Gly Phe Leu Trp Gly Met
1 5

<210> SEQ ID NO 50
<211> LENGTH: 7
<212> TYPE: PRT
<213> ORGANISM: peptide

<400> SEQUENCE: 50

Ser Arg Trp Arg Ile Leu Gly
1 5

<210> SEQ ID NO 51
<211> LENGTH: 7
<212> TYPE: PRT
<213> ORGANISM: peptide

<400> SEQUENCE: 51

His Lys Trp Gln Lys Arg Gln
1 5

<210> SEQ ID NO 52
<211> LENGTH: 7
<212> TYPE: PRT
<213> ORGANISM: peptide

<400> SEQUENCE: 52

Met Asp Pro Trp Gly Gly Trp
1 5

<210> SEQ ID NO 53
<211> LENGTH: 7
<212> TYPE: PRT
<213> ORGANISM: peptide

<400> SEQUENCE: 53

-continued

Arg Lys Val Trp Asp Ile Arg
1 5

<210> SEQ ID NO 54
<211> LENGTH: 6
<212> TYPE: PRT
<213> ORGANISM: peptide

<400> SEQUENCE: 54

Val Trp Asp His Gly Val
1 5

<210> SEQ ID NO 55
<211> LENGTH: 10
<212> TYPE: PRT
<213> ORGANISM: peptide

<400> SEQUENCE: 55

Cys Trp Gln Leu Gly Arg Asn Trp Ile Cys
1 5 10

<210> SEQ ID NO 56
<211> LENGTH: 10
<212> TYPE: PRT
<213> ORGANISM: peptide

<400> SEQUENCE: 56

Cys Val Glu Val Gln Ile Thr Gln Glu Cys
1 5 10

<210> SEQ ID NO 57
<211> LENGTH: 10
<212> TYPE: PRT
<213> ORGANISM: peptide

<400> SEQUENCE: 57

Cys Ala Gly Lys Ala Ser Ser Leu Trp Cys
1 5 10

<210> SEQ ID NO 58
<211> LENGTH: 10
<212> TYPE: PRT
<213> ORGANISM: peptide

<400> SEQUENCE: 58

Cys Arg Ala Leu Asp Ser Ala Leu Ala Cys
1 5 10

<210> SEQ ID NO 59
<211> LENGTH: 9
<212> TYPE: PRT
<213> ORGANISM: peptide

<400> SEQUENCE: 59

Cys Tyr Gly Phe Glu Ala Ala Trp Cys
1 5

<210> SEQ ID NO 60
<211> LENGTH: 9
<212> TYPE: PRT
<213> ORGANISM: peptide

<400> SEQUENCE: 60

Cys Tyr Gly Phe Leu Trp Gly Met Cys
1 5

-continued

<210> SEQ ID NO 61
<211> LENGTH: 9
<212> TYPE: PRT
<213> ORGANISM: peptide

<400> SEQUENCE: 61

Cys Ser Arg Trp Arg Ile Leu Gly Cys
1               5

<210> SEQ ID NO 62
<211> LENGTH: 9
<212> TYPE: PRT
<213> ORGANISM: peptide

<400> SEQUENCE: 62

Cys His Lys Trp Gln Lys Arg Gln Cys
1               5

<210> SEQ ID NO 63
<211> LENGTH: 9
<212> TYPE: PRT
<213> ORGANISM: peptide

<400> SEQUENCE: 63

Cys Met Asp Pro Trp Gly Gly Trp Cys
1               5

<210> SEQ ID NO 64
<211> LENGTH: 9
<212> TYPE: PRT
<213> ORGANISM: peptide

<400> SEQUENCE: 64

Cys Arg Lys Val Trp Asp Ile Arg Cys
1               5

<210> SEQ ID NO 65
<211> LENGTH: 8
<212> TYPE: PRT
<213> ORGANISM: peptide

<400> SEQUENCE: 65

Cys Val Trp Asp His Gly Val Cys
1               5

<210> SEQ ID NO 66
<211> LENGTH: 13
<212> TYPE: PRT
<213> ORGANISM: peptide

<400> SEQUENCE: 66

Cys Gly Gln Met Cys Thr Val Trp Cys Ser Ser Gly Cys
1               5                   10

<210> SEQ ID NO 67
<211> LENGTH: 7
<212> TYPE: PRT
<213> ORGANISM: peptide
<220> FEATURE:
<221> NAME/KEY: SITE
<222> LOCATION: (4)..(6)
<223> OTHER INFORMATION: X at position 4-6 is any amino acid

<400> SEQUENCE: 67

-continued

```
Gly Tyr Trp Xaa Xaa Xaa Trp
1               5


<210> SEQ ID NO 68
<211> LENGTH: 8
<212> TYPE: PRT
<213> ORGANISM: peptide
<220> FEATURE:
<221> NAME/KEY: SITE
<222> LOCATION: (4)..(6)
<223> OTHER INFORMATION: X is any amino acid
<221> NAME/KEY: SITE
<222> LOCATION: (8)..(8)
<223> OTHER INFORMATION: X is any amino acid

<400> SEQUENCE: 68

Gly Tyr Trp Xaa Xaa Xaa Trp Xaa
1               5


<210> SEQ ID NO 69
<211> LENGTH: 13
<212> TYPE: PRT
<213> ORGANISM: peptide

<400> SEQUENCE: 69

Cys Gly Gln Met Cys Thr Val Trp Cys Ser Ser Gly Ser
1               5                   10


<210> SEQ ID NO 70
<211> LENGTH: 9
<212> TYPE: PRT
<213> ORGANISM: peptide
<220> FEATURE:
<221> NAME/KEY: SITE
<222> LOCATION: (1)..(9)
<223> OTHER INFORMATION: X is any amino acid

<400> SEQUENCE: 70

Xaa Xaa Xaa Xaa Xaa Xaa Xaa Xaa Xaa
1               5


<210> SEQ ID NO 71
<211> LENGTH: 13
<212> TYPE: PRT
<213> ORGANISM: peptide
<220> FEATURE:
<221> NAME/KEY: SITE
<222> LOCATION: (2)..(4)
<223> OTHER INFORMATION: X is any amino acid
<221> NAME/KEY: SITE
<222> LOCATION: (6)..(8)
<223> OTHER INFORMATION: X is any amino acid
<221> NAME/KEY: SITE
<222> LOCATION: (10)..(12)
<223> OTHER INFORMATION: X is any amino acid

<400> SEQUENCE: 71

Cys Xaa Xaa Xaa Cys Xaa Xaa Xaa Cys Xaa Xaa Xaa Cys
1               5                   10


<210> SEQ ID NO 72
<211> LENGTH: 9
<212> TYPE: PRT
<213> ORGANISM: peptide
<220> FEATURE:
<221> NAME/KEY: SITE
<222> LOCATION: (2)..(8)
<223> OTHER INFORMATION: X is any amino acid

<400> SEQUENCE: 72
```

-continued

Cys Xaa Xaa Xaa Xaa Xaa Xaa Xaa Cys
1               5

<210> SEQ ID NO 73
<211> LENGTH: 10
<212> TYPE: PRT
<213> ORGANISM: peptide library
<220> FEATURE:
<221> NAME/KEY: SITE
<222> LOCATION: (5)..(7)
<223> OTHER INFORMATION: X is any amino acid
<221> NAME/KEY: SITE
<222> LOCATION: (9)..(9)
<223> OTHER INFORMATION: X is any amino acid

<400> SEQUENCE: 73

Cys Gly Tyr Trp Xaa Xaa Xaa Trp Xaa Cys
1               5                   10

<210> SEQ ID NO 74
<211> LENGTH: 39
<212> TYPE: DNA
<213> ORGANISM: primer
<220> FEATURE:
<221> NAME/KEY: misc_feature
<222> LOCATION: (19)..(20)
<223> OTHER INFORMATION: N= equimolar mixture of A, G, C and T
<221> NAME/KEY: misc_feature
<222> LOCATION: (21)..(21)
<223> OTHER INFORMATION: N= equimolar mixture of G and T

<400> SEQUENCE: 74
cactcggccg acggggctnn nggggccgct ggggccgaa 39

<210> SEQ ID NO 75
<211> LENGTH: 18
<212> TYPE: DNA
<213> ORGANISM: synthetic primer

<400> SEQUENCE: 75
ttcggcccca gcggcccc 18

<210> SEQ ID NO 76
<211> LENGTH: 33
<212> TYPE: DNA
<213> ORGANISM: synthetic primer

<400> SEQUENCE: 76
cctgggatcc ctggtgagtg gctactccat gac 33

<210> SEQ ID NO 77
<211> LENGTH: 32
<212> TYPE: DNA
<213> ORGANISM: synthetic primer

<400> SEQUENCE: 77
gatgaagaga tcttcatgca caatgacctc gg 32

<210> SEQ ID NO 78
<211> LENGTH: 29
<212> TYPE: DNA
<213> ORGANISM: synthetic primer

<400> SEQUENCE: 78
aggctcgagg atcctcggcc gacggggct 29

-continued

```
<210> SEQ ID NO 79
<211> LENGTH: 27
<212> TYPE: DNA
<213> ORGANISM: synthetic primer

<400> SEQUENCE: 79

aggtctagaa ttcgccccag cggcccc                                    27


<210> SEQ ID NO 80
<211> LENGTH: 19
<212> TYPE: PRT
<213> ORGANISM: peptide
<220> FEATURE:
<221> NAME/KEY: SITE
<222> LOCATION: (2)..(8)
<223> OTHER INFORMATION: X is any amino acid
<221> NAME/KEY: SITE
<222> LOCATION: (11)..(18)
<223> OTHER INFORMATION: X is any amino acid

<400> SEQUENCE: 80

Cys Xaa Xaa Xaa Xaa Xaa Xaa Xaa Cys Cys Xaa Xaa Xaa Xaa Xaa Xaa
1               5                   10                  15

Xaa Xaa Cys
```

VEGFR-3 INHIBITOR MATERIALS AND METHODS

The present application claims priority to United States provisional application entitled "VEGFR-3 INHIBITOR MATERIALS AND METHODS" filed on Jan. 17, 2001 and given the Ser. No. 60/262,476. The entire text of the aforementioned disclosure is incorporated herein by reference without prejudice or disclaimer.

FIELD OF THE INVENTION

The present invention relates to the characterization and inhibition of VEGFR-3-mediated biological activities, especially those activities which are mediated by VEGFR-3 ligands VEGF-C and/or VEGF-D. More particularly, the present invention identifies peptide inhibitors of VEGF-C or VEGF-D binding to VEGFR-3. These inhibitors may be used in methods and compositions for ameliorating the effects of VEGF-C in various disorders, as well as screening and imaging of VEGFR-3 for purposes such as research and diagnosis.

BACKGROUND OF THE INVENTION

Cancer is still a major cause of death in the world at the beginning of the 21st century and remains a major focus for ongoing research and development. In recent years a promising approach to the therapeutic intervention of cancer has focused on antiangiogenesis therapies. This approach to intervening in cancer progression takes advantage of the idea that inhibiting or otherwise limiting the blood supply to tumors will deplete the tumor of oxygen and nutrients and will cause arrest of tumor cell growth and proliferation. This approach has been found to be effective and there are presently over 20 anti-angiogenic drugs undergoing various stages of evaluation in phase I, II or III clinical trials and numerous others in preclinical development.

While there are many different forms of cancer exhibiting a wide variety of properties, one factor which many cancers share is that, in order to be fatal, they must metastasize. Until such time as metastasis occurs, a tumor, although it may be malignant, is confined to one area of the body. This may cause discomfort and/or pain, or even lead to more serious problems, nevertheless if it can be located prior to metastasis, the cancer may be managed or even removed by surgical intervention. So long as the residual cancer cells are kept in check, such a discrete cancer may be controlled without significant problems. However, metastasis will cause the cancerous cells to invaded the body and while surgical resection may remove the primary tumor, the metastatic spread of the cancer to disparate sites is very difficult to manage.

Metastasis to regional lymph nodes via lymphatic vessels is a common step in the progression of cancer. Metastasis is an important prognostic factor in many types of cancer and forms the basis for surgical and radiation treatment of local lymph nodes. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Success in establishing metastatic deposits requires tumor cells to be able to accomplish these steps sequentially.

Recently, several lines of evidences indicate that lymphangiogenesis, the formation of lymphatic vessels, promotes lymphatic metastasis (Stacker et al., Nature Med. In press (2001); Skobe et al., Nature Med. In press (2001); Mandriota et al., Nature Med. In press (2001)]. The control of lymphangiogenesis may provide a new strategy for lymph node metastasis in cancer therapy. Up to date, however, no anti-lymphangiogenic agent is known to be in clinical development.

VEGF-C was recently identified as a growth factor for the lymphatic vascular system. See International Patent Application No. PCT/US98/01973, published as WO 98/33917 on Aug. 6, 1998. One of its receptors, VEGFR-3, is expressed in all endothelial cells during early embryogenesis. During later stages of development, the expression of VEGFR-3 becomes restricted to lymphatic vessels (Alitalo et al. U.S. Pat. Nos. 6,107,046 and 5,776,755; Joukov et al., EMBO J. 15, 290-298 (1996); Aprelikov et al., Cancer Res. 52, 746-748 (1992). VEGF-C stimulates lymphangiogenesis in vivo, and transgenic mice overexpressing VEGF-C in the skin are characterized by specific hyperplasia of the lymphatic network. Furthermore, VEGF-C, has also been shown to induce angiogenesis in vitro and in vivo. As VEGFR-3 was also reported to be up-regulated on tumor blood vessels, the present inventors suggest that signaling via VEGFR-3 may stimulate both tumor lymphangiogenesis and angiogenesis (International Patent Application No. PCT/US99/23525, published as WO 00/21560, incorporated herein by reference; Valtola et al., Am. J. Pathol. 154 1382-1390 (1999) Kubo et al., Blood 96, 546-553 (2000).

A large family of vascular endothelial growth factors have been identified which, together with their receptors, play important roles in both vasculogenesis and angiogenesis [Risau et al., *Dev Biol* 125:441-450 (1988); Zachary, *Intl J Biochem Cell Bio* 30:1169-1174 (1998); Neufeld et al., *FASEB J* 13:9-22 (1999); Ferrara, *J Mol Med* 77:527-543 (1999)]. Both processes depend on the tightly controlled endothelial cell proliferation, migration, differentiation, and survival. In addition to playing a key role in the progression of cancer, dysfunction of the endothelial cell regulatory system also is involved in several diseases associated with abnormal angiogenesis, such as proliferative retinopathies, age-related muscular degeneration, rheumatoid arthritis, and psoriasis.

In addition to VEGF-C (see e.g., GenBank Acc. No. X94216; also known as VEGF related protein (VRP) or VEGF-2), the PDGF/VEGF family of growth factors also includes at least the following members: PDGF-A (see e.g., GenBank Acc. No. X06374), PDGF-B (see e.g., GenBank Acc. No. M12783), VEGF (see e.g., GenBank Acc. No. Q16889 referred to herein for clarity as VEGF-A or by particular isoform), PlGF (see e.g., GenBank Acc. No. X54936 placental growth factor), VEGF-B (see e.g., GenBank Acc. No. U48801; also known as VEGF-related factor (VRF)), VEGF-D (also known as c-fos-induced growth factor (FIGF); see e.g., Genbank Acc. No. AJ000185), VEGF-E (also known as NZ7 VEGF or OV NZ7; see e.g., GenBank Acc. No. S67522), NZ2 VEGF (also known as OV NZ2; see e.g., GenBank Acc. No. S67520), D1701 VEGF-like protein (see e.g., GenBank Acc. No. AF106020; Meyer et al., *EMBO J* 18:363-374), and NZ1O VEGF-like protein (described in International Patent Application PCT/US99/25869) [Stacker and Achen, *Growth Factors* 17:1-11 (1999); Neufeld et al., *FASEB J* 13:9- 22 (1999); Ferrara, *J Mol Med* 77:527-543 (1999)].

Members of the PDGF/VEGF family are characterized by a number of structural motifs including a conserved PDGF motif defined by the sequence: P-[PS]-C-V-X(3)-R-C-

[GSTA]-G-C-C (SEQ ID NO: 1). The brackets indicate that this position within the polypeptide can be any one of the amino acids contained within the brackets. The number contained within the parentheses indicates the number of amino acids that separate the "V" and "R" residues. This conserved motif falls within a large domain of 70-150 amino acids defined in part by eight highly conserved cysteine residues that form inter- and intramolecular disulfide bonds. This domain forms a cysteine knot motif composed of two disulfide bonds which form a covalently linked ring structure between two adjacent β strands, and a third disulfide bond that penetrates the ring [see for example, FIG. 1 in Muller et al., *Structure* 5:1325-1338 (1997)], similar to that found in other cysteine knot growth factors, e.g., transforming growth factor-β (TGF-β). The amino acid sequence of all known PDGF/VEGF proteins, with the exception of VEGF-E, contains the PDGF domain. The PDGF/VEGF family proteins are predominantly secreted glycoproteins that form either disulfide-linked or non-covalently bound homo- or heterodimers whose subunits are arranged in an anti-parallel manner [Stacker and Achen, *Growth Factors* 17:1-11 (1999); Muller et al., *Structure* 5:1325-1338 (1997)].

The PDGF subfamily is reviewed in Heldin et al., *Biochimica et Biophysica Acta* 1378:F79-113 (1998).

The VEGF subfamily is composed of PDGF/VEGF members which share a VEGF homology domain (VHD) characterized by the sequence: C-X(22-24)-P-[PSR]-C-V-X(3)-R-C-[GSTA]-G-C-C-X(6)-C-X(32-41)-C (SEQ ID NO: 2-31). The VHD domain, determined through analysis of the VEGF subfamily members, comprises the PDGF motif but is more specific.

VEGF-C, comprises a VHD that is approximately 30% identical at the amino acid level to VEGF-A (discussed below). VEGF-C is originally expressed as a larger precursor protein, prepro-VEGF-C, having extensive amino- and carboxy-terminal peptide sequences flanking the VHD, with the C-terminal peptide containing tandemly repeated cysteine residues in a motif typical of Balbiani ring 3 protein. Prepro-VEGF-C undergoes extensive proteolytic maturation involving the successive cleavage of a signal peptide, the C-terminal pro-peptide, and the N-terminal pro-peptide. Secreted VEGF-C protein consists of a non-covalently-linked homodimer, in which each monomer contains the VHD. The intermediate forms of VEGF-C produced by partial proteolytic processing show increasing affinity for the VEGFR-3 receptor, and the mature protein is also able to bind to the VEGFR-2 receptor. [International Patent Publication No. WO 98/33917; Joukov et al., *EMBO J.,* 16:(13):3898-3911 (1997).] It has also been demonstrated that a mutant VEGF-C, in which a single cysteine at position 156 is either substituted by another amino acid or deleted, loses the ability to bind VEGFR-2 but remains capable of binding and activating VEGFR-3 [International Patent Publication No. WO 98/33917]. In mouse embryos, VEGF-C mRNA is expressed primarily in the allantois, jugular area, and the region of metanephros. [Joukov et al., *J Cell Physiol* 173:211-215 (1997)]. VEGF-C is involved in the regulation of lymphatic angiogenesis: when VEGF-C was overexpressed in the skin of transgenic mice, a hyperplastic lymphatic vessel network was observed, suggesting that VEGF-C induces lymphatic growth [Jeltsch et al., *Science,* 276:1423-1425 (1997)]. VEGF-C also shows angiogenic properties: it can stimulate migration of bovine capillary endothelial (BCE) cells in collagen and promote growth of human endothelial cells [see, e.g., International Patent Publication No. WO 98/33917, incorporated herein by reference].

VEGF-D is structurally and functionally most closely related to VEGF-C [see International Patent Publ. No. WO 98/07832, incorporated herein by reference]. Like VEGF-C, VEGF-D is initially expressed as a prepro-peptide that undergoes N-terminal and C-terminal proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-DΔNΔC, is described in International Patent Publication No. WO 98/07832, incorporated herein by reference. VEGF-DΔNΔC consists of amino acid residues 93 to 201 of VEGF-D linked to the affinity tag peptide FLAG®.

VEGF-A (also known as vascular permeability factor (VPF)), was originally purified on the basis of its mitogenic activity toward endothelial cells, and also its ability to induce microvascular permeability. Further information regarding the role of VEGF-A in various biological processes may be found in for example, Ferrara,( *J Mol Med* 77: 527-543, 1999); Neufeld et al., (*FASEB J* 13: 9-22, 1999); Zachary, (*Intl J Biochem Cell Bio* 30: 1169-1174, 1998). VEGF-A is a secreted, disulfide-linked homodimeric glycoprotein composed of 23 kD subunits and five human isoforms have been described (Ferrara, *J Mol Med* 77:527-543; 1999); Neufeld et al., *FASEB J* 13:9-22; 1999). P1GF, a second member of the VEGF subfamily, is generally a poor stimulator of angiogenesis and endothelial cell proliferation in comparison to VEGF-A For additional information regarding this factor those of skill in the art are referred to, for example, Hauser et al., (*Growth Factors* 9:259-268, 1993); Maglione et al., (*Oncogene* 8:925-931, 1993) and Stacker and Achen, (*Growth Factors* 17:1-11; 1999).

VEGF-B, described in detail in International Patent Publication No. WO 96/26736 and U.S. Pat. Nos. 5,840,693 and 5,607,918, shares approximately 44% amino acid identity with VEGF-A. VEGF-B has been shown to have angiogenic properties, and may also be involved in cell adhesion and migration, and in regulating the degradation of extracellular matrix. VEGF-B is expressed primarily in embryonic and adult cardiac and skeletal muscle tissues [Joukov et al., *J Cell Physiol* 173:211-215 (1997); Stacker and Achen, *Growth Factors* 17: 1-11 (1999)]. Mice lacking VEGF-B survive but have smaller hearts, dysfunctional coronary vasculature, and exhibit impaired recovery from cardiac ischemia [Bellomo et al., Circ Res 2000;E29-E35].

Four additional members of the VEGF subfamily have been identified in poxviruses, which infect humans, sheep and goats [Ferrara, *J Mol Med* 77:527-543 (1999); Stacker and Achen, *Growth Factors* 17:1-11 (1999)]. VEGF-like proteins have also been identified from two additional strains of the orf virus, D1701 [GenBank Acc. No. AF106020; described in Meyer et al., *EMBO J* 18:363-374 (1999)] and NZ10 [described in International Patent Application PCT/US99/25869, incorporated herein by reference]. These viral VEGF-like proteins have been shown to bind VEGFR-2 present on host endothelium, and this binding is important for development of infection and viral induction of angiogenesis [Meyer et al., *EMBO J* 18:363-374 (1999); International Patent Application PCT/US99/25869].

The members of the PDGF/VEGF family are known to bind to cell surface receptors. Several such receptors have been identified, including for example, PDGFR-α (see e.g., GenBank Acc. No. NM006206), PDGFR-β (see e.g., GenBank Acc. No. NM002609), VEGFR-1/F1t-1 (fms-like tyrosine kinase-1; GenBank Acc. No. X51602; De Vries et al., *Science* 255:989-991 (1992)); VEGFR-2/KDR/F1k-1 (kinase insert domain containing receptor/fetal liver kinase-1; GenBank Acc. Nos. X59397 (F1k-1) and L04947 (KDR); Terman et al., *Biochem Biophys Res Comm* 187:1579-1586 (1992); Matthews et al., *Proc Natl Acad Sci USA* 88:9026-9030 (1991)); VEGFR-3/F1t4 (fms-like tyrosine kinase 4; U.S. Pat. No. 5,776,755 and GenBank Acc. No. X68203 and S66407; Pajusola et al., *Oncogene* 9:3545-3555 (1994)), neuropilin-1 (Gen Bank Acc. No. NM003873), and neuropilin-2 (Gen Bank Acc. No. NM003872). The two PDGF receptors mediate signaling of PDGFs as described above. $VEGF_{121}$, $VEGF_{165}$, VEGF-B, PlGF-1 and P1GF-2 bind VEGF-R1; $VEGF_{121}$, $VEGF_{145}$, $VEGF_{165}$, VEGF-C, VEGF-D, VEGF-E, and NZ2 VEGF bind VEGF-R2; VEGF-C and VEGF-D bind VEGFR-3; $VEGF_{165}$, P1GF-2, and NZ2 VEGF bind neuropilin-1; and $VEGF_{165}$, binds neuropilin-2.[Neufeld et al., *FASEB J* 13:9-22 (1999); Stacker and Achen, *Growth Factors* 17:1-11 (1999); Ortega et al., *Fron Biosci* 4:141-152 (1999); Zachary, *Intl JBiochem Cell Bio* 30:1169-1174 (1998); Petrova et al., *Exp Cell Res* 253:117-130 (1999)].

The PDGF receptors are protein tyrosine kinase receptors (PTKs) that contain five immunoglobulin-like loops in their extracellular domains. VEGFR-1, VEGFR-2, and VEGFR-3 comprise a subgroup of the PDGF subfamily of PTKs, distinguished by the presence of seven Ig domains in their extracellular domain and a split kinase domain in the cytoplasmic region. Both neuropilin-1 and neuropilin-2 are non-PTK VEGF receptors. NP-1 has an extracellular portion which includes a MAM domain; regions of homology to coagulation factors V and VIII, MFGPs and the DDR tyrosine kinase; and two CUB-like domains.

Several of the VEGF receptors are expressed as more than one isoform. A soluble isoform of VEGFR-1 lacking the seventh Ig-like loop, transmembrane domain, and the cytoplamic region is expressed in human umbilical vein endothelial cells. This VEGFR-1 isoform binds VEGF-A with high affinity and is capable of preventing VEGF-A-induced mitogenic responses [Ferrara, *J Mol Med* 77:527-543 (1999); Zachary, *Intl J Biochem Cell Bio* 30:1169-1174 (1998)]. A C-terminal truncated from of VEGFR-2 has also been reported [Zachary, *Intl J Biochem Cell Bio* 30:1169-1174 (1998)]. In humans, there are two isoforms of the VEGFR-3 protein which differ in the length of their C-terminal ends. Studies suggest that the longer isoform is responsible for most of the biological properties of VEGFR-3.

The receptors for the PDGFs, PDGF α-receptor (PDGFR-α) and the β-receptor (PDGFR-β), are expressed by many in vitro grown cell lines, and they are mainly expressed by mesenchymal cells in vivo (reviewed in [Raines et al., Peptide growth factors and their receptors, Heidelberg, Springer-Verlag (1990)]. As mentioned above, PDGF-B binds both PDGFRs, while PDGF-A selectively binds PDGFR-α.

Gene targeting studies in mice have revealed distinct physiological roles for the PDGF receptors despite the overlapping ligand specificities of the PDGFRs [Rosenkranz et al., *Growth Factors* 16:201-16 (1999)]. Homozygous null mutations for either of the two PDGF receptors are lethal. PDGFR-α deficient mice die during embryogenesis and show incomplete cephalic closure, impaired neural crest development, cardiovascular defects, skeletal defects, and odemas. The PDGFR-β deficient mice develop similar phenotypes to animals deficient in PDGF-B, that are characterized by renal, hematological and cardiovascular abnormalities; where the renal and cardiovascular defects, at least in part, are due to the lack of proper recruitment of mural cells (vascular smooth muscle cells, pericytes or mesangial cells) to blood vessels.

The expression of VEGFR-1 occurs mainly in vascular endothelial cells, although some may be present on monocytes, trophoblast cells, and renal mesangial cells [Neufeld et al., *FASEB J* 13:9-22 (1999)]. VEGFR-1-/- mice die in utero between day 8.5 and 9.5. Although endothelial cells developed in these animals, the formation of functional blood vessels was severely impaired, suggesting that VEGFR-1 may be involved in cell-cell or cell-matrix interactions associated with cell migration. Recently, it has been demonstrated that mice expressing a mutated VEGFR-1 in which only the tyrosine kinase domain was missing show normal angiogenesis and survival, suggesting that the signaling capability of VEGFR-1 is not essential. [Hiratsuka et al., Proc. Natl Acad. Sci USA 95: 9349-9354 (1998); Neufeld et al., *FASEB J* 13:9-22 (1999); Ferrara, *J Mol Med* 77:527-543 (1999)].

VEGFR-2 expression is similar to that of VEGFR-1 in that it is broadly expressed in the vascular endothelium, but it is also present in hematopoietic stem cells, megakaryocytes, and retinal progenitor cells [Neufeld et al., *FASEB J* 13:9-22 (1999)]. Although the expression pattern of VEGFR-1 and VEGFR-2 overlap extensively, evidence suggests that, in most cell types, VEGFR-2 is the major receptor through which most of the VEGFs exert their biological activities. Examination of mouse embryos deficient in VEGFR-2 further indicate that this receptor is required for both endothelial cell differentiation and the development of hematopoietic cells [Joukov et al., *J Cell Physiol* 173:211-215 (1997)].

VEGFR-3, described in detail in U.S. Pat. Nos. 5,776,755 and 6,107,046, incorporated here by reference, is expressed broadly in endothelial cells during early embryogenesis. During later stages of development, the expression of VEGFR-3 becomes restricted to developing lymphatic vessels [Kaipainen, A., et al., *Proc. Natl. Acad. Sci. USA,* 92: 3566-3570 (1995)]. In adults, the lymphatic endothelia and some high endothelial venules express VEGFR-3, and increased expression occurs in lymphatic sinuses in metastatic lymph nodes and in lymphangioma. VEGFR-3 is also expressed in a subset of $CD34^+$ hematopoietic cells which may mediate the myelopoietic activity of VEGF-C demonstrated by overexpression studies [WO 98/33917]. Targeted disruption of the VEGFR-3 gene in mouse embryos leads to failure of the remodeling of the primary vascular network, and death after embryonic day 9.5 [Dumont et al., Science, 282: 946-949 (1998)]. These studies suggest an essential role for VEGFR-3 in the development of the embryonic vasculature, and also during lymphangiogenesis.

Structural analyses of the VEGF receptors indicate that the VEGF-A binding site on VEGFR-1 and VEGFR-2 is located in the second and third Ig-like loops. Similarly, the VEGF-C and VEGF-D binding sites on VEGFR-2 and VEGFR-3 are also contained within the second Ig-loop [Taipale et al., *Curr Top Microbiol Immunol* 237:85-96 (1999)]. The second Ig-like loop also confers ligand specificity as shown by domain swapping experiments [Ferrara, *J Mol Med* 77:527-543 (1999)]. Receptor-ligand studies indicate that dimers formed by the VEGF family proteins are capable of binding two VEGF receptor molecules, thereby dimerizing VEGF receptors. The fourth Ig-like domain on VEGFR-1, and also possibly on VEGFR-2, acts as the receptor dimerization domain that links two receptor molecules upon binding of the receptors to a ligand dimer [Ferrara, *J Mol Med* 77:527-543 (1999)]. Although the regions of VEGF-A that bind VEGFR-1 and VEGFR-2 overlap to a large extent, studies have revealed two separate domains within VEGF-A that interact with either VEGFR-1 or VEGFR-2, as well as specific amino acid residues within these domains that are critical for ligand-receptor interactions. Mutations within either VEGF receptor-specific domain that specifically prevent binding to one particular VEGF receptor have also been recovered [Neufeld et al., *FASEB J* 13:9-22 (1999)].

VEGFR-1 and VEGFR-2 are structurally similar, share common ligands ($VEGF_{121}$ and $VEGF_{165}$), and exhibit similar expression patterns during development. However, the signals mediated through VEGFR-1 and VEGFR-2 by the same ligand appear to be slightly different. VEGFR-2 has been shown to undergo autophosphorylation in response to VEGF-A, but phosphorylation of VEGFR-1 under identical conditions was barely detectable. VEGFR-2 mediated signals cause striking changes in the morphology, actin reorganization, and membrane ruffling of porcine aortic endothelial cells recombinantly overexpressing this receptor. In these cells, VEGFR-2 also mediated ligand-induced chemotaxis and mitogenicity; whereas VEGFR-1-transfected cells lacked mitogenic responses to VEGF-A. Mutations in VEGF-A that disrupt binding to VEGFR-2 fail to induce proliferation of endothelial cells, whereas VEGF-A mutants that are deficient in binding VEGFR-1 are still capable of promoting endothelial proliferation. Similarly, VEGF stimulation of cells expressing only VEGFR-2 leads to a mitogenic response whereas comparable stimulation of cells expressing only VEGFR-1 also results in cell migration, but does not induce cell proliferation. In addition, phosphoproteins co-precipitating with VEGFR-1 and VEGFR-2 are distinct, suggesting that different signaling molecules interact with receptor-specific intracellular sequences.

The emerging hypothesis is that the primary function of VEGFR-1 in angiogenesis may be to negatively regulate the activity of VEGF-A by binding it and thus preventing its interaction with VEGFR-2, whereas VEGFR-2 is thought to be the main transducer of VEGF-A signals in endothelial cells. In support of this hypothesis, mice deficient in VEGFR-1 die as embryos while mice expressing a VEGFR-1 receptor capable of binding VEGF-A but lacking the tyrosine kinase domain survive and do not exhibit abnormal embryonic development or angiogenesis. In addition, analyses of VEGF-A mutants that bind only VEGFR-2 show that they retain the ability to induce mitogenic responses in endothelial cells. However, VEGF-mediated migration of monocytes is dependent on VEGFR-1, indicating that signaling through this receptor is important for at least one biological function. In addition, the ability of VEGF-A to prevent the maturation of dendritic cells is also associated with VEGFR-1 signaling, suggesting that VEGFR-1 may function in cell types other than endothelial cells. [Ferrara, *J Mol Med* 77:527-543 (1999); Zachary, *Intl J Biochem Cell Bio* 30:1169-1174 (1998)].

Neuropilin-1 was originally cloned as a receptor for the collapsin/semaphorin family of proteins involved in axon guidance [Stacker and Achen, *Growth Factors* 17:1-11 (1999)]. It is expressed in both endothelia and specific subsets of neurons during embryogenesis, and it thought to be involved in coordinating the developing neuronal and vascular system. Although activation of neuropilin-1 does not appear to elicit biological responses in the absence of the VEGF family tyrosine-kinase receptors, the presence of neuropilins on cells leads to more efficient binding of $VEGF_{165}$ and VEGFR-2 mediated responses. [Neufeld et al., *FASEB J* 13:9-22 (1999)] Mice lacking neuropilin-1 show abnormalities in the developing embryonic cardiovascular system. [Neufeld et al., *FASEB J* 13:9-22 (1999)]

Neuropilin-2 was identified by expression cloning and is a collapsin/semaphorin receptor closely related to neuropilin-1. Neuropilin-2 is an isoform-specific VEGF receptor in that it only binds $VEGF_{165}$. Like neuropilin-1, neuropilin-2 is expressed in both endothelia and specific neurons, and is not predicted to function independently due to its relatively short intracellular domain. The function of neuropilin-2 in vascular development is unknown [Neufeld et al., *FASEB J* 13:9-22 (1999); WO 99/30157].

The discovery of VEGF-A as a key regulator of vascular development has spurred active research using VEGF-based therapeutic angiogenesis in cardiovascular medicine, as well as for treating diseases characterized by pathological angiogenesis with VEGF antagonists. Subsequent identification of additional VEGF family proteins and their roles in vascularization have also led to the development of therapies based on these growth factors [Ferrara and Alitalo, *Nature Med* 5:1359-1364 (1999)]. Animal studies of hindlimb ischemia, and myocardial ischemia using VEGF-A or VEGF-C, delivered by administration of recombinant protein or gene transfer using naked DNA or adenoviral vectors, implicate these molecules in promoting vascularization and increasing coronary blood flow.

Therapies based on inhibiting the activity of VEGF growth factors are being tested to treat disease states characterized by pathological angiogenesis. VEGF expression is upregulated in many human tumors including primary breast cancer and gastric carcinoma. Studies in mice indicate that tumor-associated angiogenesis and growth of the tumor cells can be inhibited by treating the animals with monoclonal antibodies against VEGF-A. Further animal studies showed that expression of a dominant negative VEGFR-2 mutant that prevents signaling through this receptor, or administration of recombinant VEGFR-1 or VEGFR-2 mutants, which only contain the extracellular portion of these receptors, suppresses growth of several tumor cell lines. These encouraging results led to clinical trials using humanized high affinity monoclonal antibodies against VEGF-A (rhuMAb VEGF) as VEGF-A inhibitors. Phase II studies using rhuMAb VEGF to treat non-small cell lung carcinoma, colorectal carcinoma, breast, and renal cell carcinoma are currently ongoing. Compounds targeting inhibition of VEGF-A activity are also being tested for therapeutic uses in cancer patients: small molecule inhibitors of VEGF-A are in Phase II trials, and monoclonal antibodies against VEGFR-2 are entering clinical trials.

Retinopathy associated with diabetes mellitus, occlusion of central retinal vein or prematurity has been correlated with increased levels of VEGF-A. Animal studies using monoclonal antibodies against VEGF-A or soluble VEGFR-1 or VEGFR-2 mutants containing only the extracellular domain fused to immunoglobulin gFc domain show suppression of retinal angiogenesis. VEGF-A is also detected in age-related macular degeneration (AMD), and its expression is thought to be the cause of neovascularization in this disease. Intravitreal delivery of recombinant humanized anti-VEGF-A Fab antibody fragment or injection of 2'-fluoropyrimidine RNA oligonucleotide ligands (aptamers) to treat AMD are currently in clinical trials. Compounds that inhibit the activity of VEGF growth factors may also be used to treat other disease states involving abnormal angiogenesis. These include ischemic-reperfusion related brain edema and injury, conditions associated with ovarian hyperplasia and hypervascularity such as the polycystic ovary syndrome, endometriosis, and ovarian hyperstimulation syndrome [Ferrara and Alitalo, *Nature Med* 5:1359-1364 (1999)].

From the foregoing discussion, it will be apparent that inhibitors of the VEGF family, have tremendous potential as therapeutics, and new agents of this type represent a continuing need in the art for inhibiting neovascularization in the inhibition or elimination of a variety of neoplastic disorders or cell proliferative disorders.

SUMMARY OF THE INVENTION

The present invention provides materials and methods that satisfy one or more needs in the art described above. In particular, the present invention provides binding compounds for members of the VEGF receptor family, especially compounds that bind VEGFR-3, and including compounds that inhibit ligand-mediated stimulation of VEGFR-3 activity. Many uses of such compounds, for screening samples, imaging, diagnosis, and therapy, are also provided.

For example, in one embodiment, the invention provides an isolated peptide comprising the formula: $X_1X_2X_3X_4X_5X_6X_7X_8$ (SEQ ID NO: 32), wherein $X_1$ through $X_8$ are amino acid residues, wherein the peptide binds to VEGFR3, and wherein $X_1$ through $X_8$ are defined as follows: the amino acid residue at $X_1$ is a glycine residue or a conservative substitution thereof; the amino acid residue at $X_2$ is a tyrosine residue or a conservative substitution thereof; the amino acid residue at $X_3$ is a tryptophan residue or a conservative substitution thereof; the amino acid residue at $X_4$ is a leucine residue or a conservative substitution thereof; the amino acid residue at $X_5$ is a threonine residue or a conservative substitution thereof; the amino acid residue at $X_6$ is an isoleucine residue or a conservative substitution thereof; the amino acid residue at $X_7$ is a tryptophan residue or a conservative substitution thereof; and the amino acid residue at $X_8$ is a glycine residue or a conservative substitution thereof. The term peptide encompasses amino acid polymers, optionally including additional substituents as described below. However, the definition of peptide is intended to exclude naturally occurring polypeptide sequences that were described in the scientific literature before Jan. 17, 2001, and that fortuitously share amino acid sequence identity with the peptide sequences described herein. Preferred peptides are from 6 to 100 amino acids in length, e.g., 6, 7, 8, 9, 10, 11, 12, . . . 97, 98, 99, or 100 amino acids in length. Although peptide sequences are often described herein as linear sequences from the amino-terminus to the carboxy-terminus, it is contemplated that the peptides may be made cyclic by the formation of at least one bond between non-adjacent amino acids. For example, in one variation, the peptides are formed with terminal cysteines which can be made to form an intramolecular disulfide bond. Thus, in one preferred embodiment, the peptide further comprises amino- and carboxy- terminal cysteine residues. For example, the peptide may comprise the amino acid sequence: $CX_1X_2X_3X_4X_5X_6XX_7X_8C$ (SEQ ID NO: 33), wherein $X_1X_2X_3X_4X_5X_6X_7X_8$ (SEQ ID NO: 32) are defined as above, and C represents cysteine. In an alternative embodiment, additional residues are attached to $X_1$ or $X_8$, within the terminal cysteines.

Preferred conservative substitutions for these peptide molecules include any of the following, in any combination: the conservative substitution at position $X_1$ is selected from isoleucine, valine, leucine, alanine, cysteine, phenylalanine, proline, tryptophan, tyrosine, norleucine and methionine; the conservative substitution at position $X_2$ is selected from isoleucine, valine, leucine, alanine, cysteine, glycine, phenylalanine, proline, tryptophan, norleucine and methionine; the conservative substitution at position $X_3$ is selected from isoleucine, valine, leucine, alanine, cysteine, glycine, phenylalanine, proline, tyrosine, norleucine and methionine; the conservative substitution at position $X_4$ is selected from isoleucine, valine, alanine, cysteine, glycine, phenylalanine, proline, tryptophan, tyrosine, norleucine and methionine; the conservative substitution at position $X_5$ is selected from asparagine, glutamine, and serine; the conservative substitution at position $X_6$ is selected from valine, leucine, alanine, cysteine, glycine, phenylalanine, proline, tryptophan, tyrosine, norleucine or methionine; the conservative substitution at position $X_7$ is selected from isoleucine, valine, leucine, alanine, cysteine, glycine, phenylalanine, proline, tyrosine, norleucine and methionine; and the conservative substitution at position $X_8$ is selected from isoleucine, valine, leucine, alanine, cysteine, phenylalanine, proline, tryptophan, tyrosine, norleucine and methionine.

In preferred embodiments, only one, two, or three conserved amino acid substitutions are introduced at any one time at the eight enumerated positions.

In on preferred embodiments, the invention provides an isolated peptide comprising the sequence $Y_1$GYWLTIWG$Y_2$ (SEQ ID NO: 34), wherein $Y_1$ and $Y_2$ are amino acids. In one variation, the peptide is made cyclic by a bond between $Y_1$ and $Y_2$. In a specific preferred embodiment, the peptide comprises the sequence CGYWLTIWGC (SEQ ID NO: 35).

Initial screening has identified other promising VEGFR-3 binding peptides as well. For example, the invention provides a peptide comprising any of the following amino acid sequences: SGYWWDTWF (SEQ ID NO: 36), SCYWRDTWF (SEQ ID NO: 37), KVGWSSPDW (SEQ ID NO: 38), FVGWTKVLG (SEQ ID NO: 39), YSSSMRWRH (SEQ ID NO: 40), RWRGNAYPG (SEQ ID NO: 41), SAVFRGRWL (SEQ ID NO: 42), WFSASLRFR (SEQ ID NO: 43), and conservative substitution-analogs thereof, wherein the peptide binds human VEGFR-3. Preferred peptides comprise these exact amino acid sequences, or sequences in which only one or only two conserved substitutions have been introduced. In another preferred variation, the peptides are preferred with amino- and carboxy- terminal cysteines, which permit formation of cyclic molecules and dimers and multimers.

By way of another example, the invention provides a peptide comprising any of the following amino acid sequences: WQLGRNWI (SEQ ID NO: 44), VEVQITQE (SEQ ID NO: 45), AGKASSLW (SEQ ID NO: 46), RALDSALA (SEQ ID NO: 47), YGFEAAW (SEQ ID NO: 48), YGFLWGM (SEQ ID NO: 49), SRWRILG (SEQ ID NO: 50), HKWQKRQ (SEQ ID NO: 51), MDPWGGW (SEQ ID NO: 52), RKVWDIR (SEQ ID NO: 53), VWDHGV (SEQ ID NO: 54), and conservative substitution-analogs thereof, wherein the peptide binds human VEGFR-3. Preferred peptides comprise these exact amino acid sequences, or sequences in which only one or only two conserved substitutions have been introduced. In another preferred variation, the peptides are preferred with amino- and carboxy-terminal cysteines, which permit formation of cyclic molecules and dimers and multimers. For example, the invention provides peptides that bind VEGFR-3 and comprise the following sequences: CWQLGRNWIC (SEQ ID NO: 55), CVEVQITQEC (SEQ ID NO: 56), CAGKASSLWC (SEQ ID NO: 57), CRALDSALAC (SEQ ID NO: 58), CYGFEAAWC (SEQ ID NO: 59), CYGFLWGMC (SEQ ID NO: 60), CSRWRILGC (SEQ ID NO: 61), CHKWQKRQC (SEQ ID NO: 62), CMDPWGGWC (SEQ ID NO: 63), CRKVWDIRC (SEQ ID NO: 64), CVWDHGVC (SEQ ID NO: 65).

In still another variation, the invention provides an isolated peptide that binds VEGFR-3 and that comprises the amino acid sequence CGQMCTVWCSSGC (SEQ ID NO: 66), or conservative substitutions-variants thereof.

In yet another variation, the invention provides the following genus of peptides: isolated peptides that comprise the amino acid sequence GYW$X_1X_2X_3$W (SEQ ID NO: 67), wherein $X_1$, $X_2$, and $X_3$ comprise amino acids, and wherein the peptide binds VEGFR-3. In a related embodiment, the invention provides an isolated peptide that binds VEGFR-3 and that comprises the amino acid sequence $GYWX_1X_2X_3WX_4$ (SEQ ID NO: 68), wherein $X_4$ comprises an amino acid. In still another variation, these peptides further comprising amino- and carboxy-terminal cysteine residues.

For any of the foregoing peptides, one preferred variation involves peptides that have been modified to comprise an intramolecular bond between two non-adjacent amino acid residues of the primary sequence, thereby forming a cyclic peptide. For example, in one variation, the peptide comprises a pair of cysteine residues, such as amino- and carboxy-terminal cysteines, and the intramolecular bond comprises a disulfide bond between the cysteines. However, organic chemists and peptide chemists are capable of synthesizing intramolecular bonds between a wide variety of amino acids using conventional techniques.

Any peptide that binds VEGFR-3 can be used as a reagent for detecting VEGFR-3 in a sample. For example, detection of VEGFR-3 is useful as one of a battery of markers for determining whether endothelial cells in a tissue sample are lymphatic or blood vessel endothelial cells. Detecting VEGFR-3 in samples also may have diagnostic relevance. For example, because tumor metastases appear to involve migration through blood vessels and/or the lymphatic system, the presence, quantity, and distribution of VEGFR-3 expressing endothelia in and around a tumor will often be indicative of the stage of the tumor progression and/or the aggressiveness of the tumor. Knowledge of tumor vascularization provided by VEGFR-3 imaging aids in the selection of a therapeutic regimen.

Attachment of a label such as a radionucleotide, a dye, or an enzyme or enzyme substrate aids in imaging, and peptides of the invention comprising such labels are represent another embodiment of the invention. Antibodies to peptides of the invention, represent another embodiment of the invention.

Peptides that bind and stimulate VEGFR-3 activity are useful in all manners that VEGF-C and/or VEGF-D have been described as useful, including promoting the growth of endothelial cells, treatment of ischemia or lymphedema, treatment or restenosis, or the like.

Peptides of the invention that bind VEGFR-3 and inhibits Vascular Endothelial Growth Factor C (VEGF-C) and/or Vascular Endothelial Growth Factor-D (VEGF-D) binding to VEGFR-3 represent a highly preferred class of peptides of the invention. In addition to utility for detecting, diagnosing, and imaging as mentioned above, inhibitors of ligand-mediated stimulation of VEGFR-3 can be used as therapeutics for blocking angiogenesis and lymphangiogenesis mediated through VEGFR-3. Evidence increasingly accumulates that VEGF-C/D and VEGFR-3 are implicated in these processes in tumor growth and metastases.

Although the peptide inhibitors of VEGFR-3 have therapeutic utility simply by virtue of their ability to block ligand-mediated stimulation of VEGFR-3, enhancement of this therapeutic utility is possible by delivery of additional therapeutic agents with the peptides. In one variation, peptides can be co-administered with other therapeutic agents. However, in a preferred variation, a second therapeutic agent is attached to the peptide, and the peptides affinity for VEGFR-3 assists in the targeted delivery of the second therapeutic agent to VEGFR-3 expressing cells. For example, the invention provides peptides as described above, further comprising a cytotoxic agent attached to the peptide. Exemplary cytotixic agents include radioisotopes, any known anti-neoplastic drug or pro-drug that can be administered and converted to a drug in vivo; and the like. Alternatively, the peptide is embedded in a drug-containing liposome (e.g., with a hydrophobic tail) and used to target the liposome to VEGFR-3 expressing cells.

In still another variation, the extra therapeutic is another protein, such as a tumor necrosis factor. With protein therapeutics, a preferred embodiment of the invention provides a chimeric protein comprising a therapeutic protein amino acid sequence attached to the amino acid sequence of a peptide of the invention.

In still another variation, the peptide is attached to an antibody or fragment thereof. The antibody or fragment may recognize another antigen on the target tumor or target endothelia, and/or may recognize an antigen on cytotoxic T cells or other immune cells that will help eradicate the target cells.

In still another variation, the peptides of the invention are further modified for purposes related to increased shelf-life until usage; increased stability; increased circulating in-vivo half-life of the peptide in a mammal; reduced systemic toxicity, and the like. Standard pharmaceutical and formulation chemistry is used to achieve such goals, e.g., through glycosylation, pegylation, introduction of non-hydrolyzable bonds, mixing with pharmaceutically acceptable diluents, adjuvants, or carriers, and the like. Thus, in still another embodiment, the invention provides a composition comprising an isolated peptide as described above or peptide dimer as described immediately below, in a pharmaceutically acceptable carrier. In a related embodiment, the invention provides a unit dose of the peptide, preferably contained in a container labeled with the contents of the container and instructions for administration to a subject.

In still another variation, the invention provides a peptide dimer comprising first and second peptide monomers, wherein at least one of the peptide monomers comprises a peptide as described above, and wherein the dimer binds to VEGFR-3. It is contemplated that dimers may make more potent therapeutics than monomers. The VEGFR-3 ligands VEGF-C and VEGF-D are believed to circulate as homodimers. In a preferred variation, both the first and second peptide monomer comprise peptides of the invention. In a highly preferred variation, the first and second monomers comprise the same peptide.

Additional sreening of peptides of the invention against other VEGF receptors may identify peptides that bind to multiple VEGF receptors, and thereby represent still more potent therapeutics for prevention of angiogenic and lymphangiogenic activities in vivo. In one preferred embodiment, the invention provides peptides as described above that bind at least one growth factor receptor selected from the group consisting of VEGFR-1, VEGFR-2 and neuropilin-1 (NP-1) and neuropilin-2 (NP-2). In an alternative embodiment, the peptide of the invention is used to form a dimer with a peptide that binds to at least one growth factor receptor selected from the group consisting of VEGFR-1, VEGFR-2 and neuropilin-1 (NP-1) and neuropilin-2 (NP-2), thereby forming a dimer that can bind both VEGFR-3 and another receptor.

Peptides of the invention can be made using synthetic techniques and recombinant DNA techniques. Because of the latter, the invention further provides polynucleotides comprising nucleotide sequences that encode peptides of the invention; vectors (especially expression vectors) comprising such polynucleotides; host cells comprising the polynucleotides or the vectors; and methods of making the peptides using the polynucleotides, vectors, or host cells, such as expressing the polynucleotide in a cell and purifying the resultant peptide. If the peptide is espressed as a fusion with a partner, it may be desirable to cleave the fusion to obtain purified peptide.

It will be apparent from the many uses described herein for peptides of the invention that the invention also provides a number of methods and applications involving the peptides.

For example, the invention provides a method of inhibiting the proliferation of a cell comprising contacting a cell that expresses VEGFR-3 with a peptide of the invention in an amount effective to inhibit the proliferation of the cell. Determination of the amount of peptide required to inhibit proliferation of cells can be estimated from concentrations of the peptide required to inhibit binding of the a VEGFR-3 ligand to VEGFR-3 in vitro, and/or using dose/response studies, or using other assays available in the art. Contemplated target cells known to express VEGFR-3 include endothelial cells (especially lymphatic endothelial cells), endothelial progenitor cells, and hematopoietic progenitor cells. Mammalian target cells are preferred. A number of cancer cells and cell lines express VEGFR-3 and these represent targets as well. In one preferred variation, the contacting step comprises contacting the cell with a composition comprising the peptide in a pharmaceutically acceptable carrier.

In a related embodiment, the invention provides a method for inhibiting proliferation of a cell that expresses VEGFR-3, comprising a step of contacting the cell with a nucleic acid comprising a nucleotide sequence encoding the peptide and further comprising a promoter active in the cell, wherein the promoter is operably linked to the nucleotide sequence encoding the peptide, under conditions permitting the uptake of the nucleic acid and expression of the peptide by the cell in an amount effective to inhibit the proliferation of the cell. In one variation, the nucleic acid is encapsulated in a liposome. In another variation, the nucleic acid is a viral vector selected from the group consisting of retrovirus, adenovirus, adeno-associated virus, vaccinia virus and herpesvirus.

The foregoing methods can be performed in vitro or can be performed in vivo, by administering the peptide to an organism that comprises the target cell.

In still another embodiment, the invention provides a method of treating a mammalian subject to modulate the growth in the subject of cells that express VEGFR-3, comprising administering to the mammalian subject a composition comprising a peptide of the invention. Preferably, the peptide has been formulated with a pharmaceutically acceptable carrier.

As explained above, many peptides of the invention inhibit ligand binding to VEGFR-3, making the peptides useful inhibitors. Thus, in a preferred treatment variation, the mammalian subject has been diagnosed with a disease characterized by proliferation of endothelial cells that express VEGFR-3. For example, many tumors are characterized by blood vessel or lymphatic vessel neovascularization, wherein the neovascularization comprises endothelial cells that express VEGFR-3. In some cancers, the cancer cells themselves express VEGFR-3, and represent the target cells. In another, possibly overlapping set of cancers, the cancer cells express a VEGFR-3 ligand selected from VEGF-C and VEGF-D. The ligand is believed to be involved in recruiting endothelial cells and stimulating their growth, theirby facilitating nourishment and/or spread of the cancer.

In relateds embodiment, the invention provides a method of inhibiting metastatic spread of a cancer in a mammalian subject comprising administering to a mammalian subject suspected of having cancer a peptide of the invention, in an amount effective to inhibit metastatic spread of the cancer; and a method for treating cancer comprising administering to a mammalian subject diagnosed with a cancer a composition comprising a peptide of the invention, in an amount effect to reduce growth or neoplastic spread of the cancer. It will be appreciated that any reduction in the rate of cancer growth or spread (which can prolong life and quality of life) is indicative of successful treatment. In preferred embodiments, cancer growth is halted completely. In still more preferred embodiments, cancers shrink or are eradicated entirely. Preferred subjects for treatment are human subjects, but other animals, especially murine, rat, bovine, porcine, primate. and other model systems for cancer treatment, are contemplated. Without intending to be limited to any theory, the peptides of the invention are expected to be effective at least in part because the peptides inhibit at least one of angiogenesis and lymphangiogenesis near the cancer in the subject. In some cancers that express VEGFR-3, direct inhibition of cancer growth or cancer killing may be the mechanism. Treatment of all cancers that express VEGFR-3 and all cancers characterized by angiogenesis or lymphangiogenesis in and around a growing tumor is contemplated. For example, treatment is contemplated of cancers of a tissue, organ, or cell selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood.

In a related embodiment, the invention provides a method of treating a mammalian subject having a disease characterized by proliferation of cells that express at least one of VEGFR-3, VEGF-C, and VEGF-D, comprising a step of administering to the subject a nucleic acid comprising a nucleotide sequence encoding a peptide of the invention, and further comprising a promoter, wherein the promoter is operably linked to the nucleotide sequence encoding the peptide.

The peptides of the invention merely provide one additional set of therapeutics in the arsenal against cancer. In one variation of the foregoing methods of treatment, the peptides are administered along with a second cancer therapeutic agent. The second agent can be any chemotherapeutic agent, radioactive agent, radiation, nucleic acid encoding a cancer therapeutic agent, antibody, protein, and/or other anti-lymphangiogenic agent or an anti-angiogenic agent. The second agent may be administed before, after, or concurrently with the peptide of the invention. As explained above, the second therapeutic also may be attached to the peptide of the invention to improve localization to the target tissue and/or reduce systemic toxicity.

In one variation, the subject to be treated has been diagnosed with an operable tumor, and the administering step is performed before, during, or after the tumor is resected from the subject. Peptide treatment in conjunction with tumor resection is intended to reduce or eliminate regrowth of tumors from cancer cells that fail to be resected.

Stated more generically, the invention provides a method of treating a pathology characterized by VEGFR-3 binding to a natural ligand that binds VEGFR-3, comprising the step of administering to an individual in need thereof a peptide of the invention.

Due to their receptor binding properties, peptides of the invention also are useful in non-therapeutic contexts. For example, the invention provides a method of screening a biological sample for VEGFR-3, comprising steps of: (a) contacting a biological sample suspected of containing VEGFR-3 protein with a composition comprising a peptide of the invention; and (b) determining the binding of the peptide with the receptor. Preferably, the peptide comprises a detectable label, and the determining step comprises detecting the presence, distribution, and/or quantity of the label bound to the biological sample. If the method is performed ex vivo, it may be preferable to perform a washing step to remove unbound peptide after the contacting step and prior to the determining step. In a preferred variation, the biological sample comprises mammalian cells, such as a biopsy sample from a patient.

In a related embodiment, the invention provides a method of imaging cells that express VEGFR-3 in a tissue suspected of containing cells that express VEGFR-3 comprising: (a) contacting the tissue with a composition comprising a peptide of the invention; and (b) imaging cells that express VEGFR-3 in the tissue by detecting the peptide bound to cell in the tissue. Preferably, the peptide comprises a detectable label, and the imaging step comprises detecting the label in the tissue. Optionally, an intermediate washing step is included. Preferably, the tissue imaged is human tissue, such as human tissue suspected of having neoplastic cell growth.

In still another related variation, the invention provides a method of screening for neovascularization in a tumor, comprising steps of: contacting a tissue suspected of containing a tumor with a peptide of the invention; and detecting binding of the peptide in the tissue, wherein binding of the peptide to the tissue correlates with the presence of neovascularization in the tissue. Preferably, the peptide comprises a label, and the detecting step comprises measuring the quantity and distribution of the label.

In still another related variation, the invention provides a method of diagnosing a cancer, comprising screening for neovascularization as described in any of the preceding paragraphs, wherein increased quantity and distribution of the label correlates with increased neovascularization and increased agressiveness of the tumor. A diagnosis of tumor progression and agressiveness is made from the quantity and distribution of the labeled peptide.

Additional features and variations of the invention will be apparent to those skilled in the art from the entirety of this application, and all such features are intended as aspects of the invention.

Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

Aspects of the invention may be summarized by genus, and it should be understood that every indivdual member of the genus is intended as an individual aspect of the invention.

Aspects of the invention may be described using the term "comprising" or "including" or other synonyms, and these terms are intended to represent "open" or "inclusive" language such that they include recited elements but also permit inclusion of additional, unrecited elements.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE PREFERRED EMBODIMENTS

Figure 1:
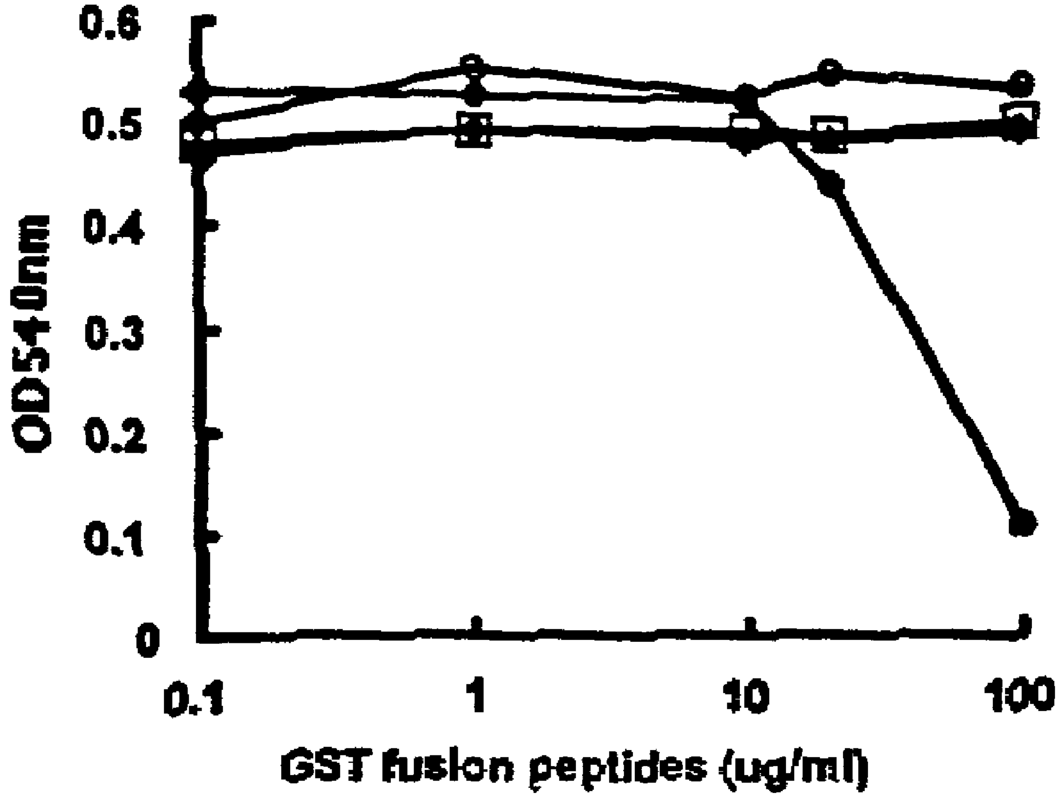
FIG. 1 depicts the effects of peptides fused to GST on the growth of BaF3-R3/EpoR. The effects were determined using an MTT cell survival assay. CGYWLTIWGC (SEQ ID NO: 35) (closed circles) is identified herein as an inhibitor of VEGF-C binding to VEGFR-3. The open circles represent the effects of CWQLGRNWIC (SEQ ID NO: 55); squares represent CGQMCTVWCSSGS (SEQ ID NO: 69) and diamonds represent a control $CX_8C$ peptide.

The present invention is related to methods and compositions for the inhibition of the interaction between VEGF-C and VEGFR-3. More specifically identified herein are peptides that are inhibitors of VEGF-C binding to VEGFR-3. Additionally it is contemplated that the inhibitors also may be inhibitors of VEGF-D binding to VEGFR-3. As such, this invention contemplates the use of these peptides in order to ameliorate disorders mediated binding between VEGFR-3 and VEGF-C/D. In specific embodiments the peptides of the invention will be useful in the inhibition of VEGF-C/D mediated cell proliferation. By "VEGF-C/D" the present specification means that the inhibitors may be inhibitors of VEGF-C and/or VEGF-D binding to VEGFR-3. The peptides of the invention may be used as anti-cancer agents that may exert their effects through an inhibition of lymphangiogenesis and/or angiogenesis. Methods and compositions for making and using the peptides of the instant invention are discussed in further detail below.

A. Novel Peptides of the Present Invention

The present invention provides novel inhibitors of VEGF-C/D binding to VEGFR-3. As descrided with particularity below, specific peptides of the present invention were identified via in vitro biopanning of phage display libraries of random peptides. Such biopanning methods have been used by the inventors previously for isolating integrin binding peptides (Koivunen et al., *Methods Mol. Biol.* 129:3-17, 1999; Koivunen et al., *Biotechnol.,* 18(8):768-74, 1999). Random $CX_8C$ (SEQ ID NO: 33), $X_9$ (SEQ ID NO: 70) and $CX_3CX_3CX_3C$ (SEQ ID NO: 71) peptide libraries comprising $10^9$ independent clones were screened by binding to immobilized VEGFR3-Fc fusion protein. Pronounced enrichment in phage binding to the VEGFR3-Fc was found in the third and fourth rounds of iterative screening as compared to control (BSA). The clones selected from the iterative screening were as listed in Table 1.

TABLE 1

| X9 (SEQ ID NO: 70) | CX8C (SEQ ID NO: 33) | CX7C (SEQ ID NO: 72) | CX3CX3CX3C (SEQ ID NO: 71) |
|---|---|---|---|
| SGYWWDTWF | CGYWLTIWGC | CYGFEAAWC | CGQMCTVWCSSG |

TABLE 1-continued

| | | | |
|---|---|---|---|
| (SEQ ID NO: 36) | (SEQ ID NO: 35) | (SEQ ID NO: 59) | C (SEQ ID NO: 66) |
| SCYWRDTWF (SEQ ID NO: 37) | CWQLGRNWIC (SEQ ID NO: 55) | CYGFLWGMC (SEQ ID NO: 60) | |
| KVGWSSPDW (SEQ ID NO: 38) | CVEVQITQEC (SEQ ID NO: 56) | CSRWRILGC (SEQ ID NO: 61) | |
| FVGWTKVLG (SEQ ID NO: 39) | CAGKASSLWC (SEQ ID NO: 57) | CHKWQKRQC (SEQ ID NO: 62) | |
| | CRALDSALAC (SEQ ID NO: 58) | CMDPWGGWC (SEQ ID NO: 63) | |
| YSSSMRWRH (SEQ ID NO: 40) | | | |
| RWRGNAYPG (SEQ ID NO: 41) | | CRKVWDIRC (SEQ ID NO: 64) | |
| | | CVWDHGVC (SEQ ID NO: 65) | |
| SAVFRGRWL (SEQ ID NO: 42) | | | |
| WFSASLRFR (SEQ ID NO: 43) | | | |

The selected phages revealed several classes of VEGFR-3 binding motifs such as, for example, GYWXXXW (SEQ ID NO: 67), VGW, RWR, VWD. The most frequent sequence was CGYWLTIWGC (SEQ ID NO: 35). The peptide sequences were compared with the primary sequence of VEGF-C (a ligand of VEGFR-3, Genbank accession number: NM_005429). However, alignment of the individual selected clones or of the consensus motifs with VEGF-C did not produce any significant homology, suggesting that the selected peptides mimicked a discontinuous binding site.

Given the above finding, a preferred peptide of the present invention comprises a formula of $$C\text{-}X_1\text{-}X_2\text{-}X_3\text{-}X_4\text{-}X_5\text{-}X_6\text{-}X_7\text{-}X_8\text{-}C \quad \text{(SEQ ID NO: 33)}$$

in which $X_1$ through X8 are amino acid residues wherein the $X_1$ is a glycine residue or a conservative substitution thereof: $X_2$ is a tyrosine residue or a conservative substitution thereof; $X_3$ is a tryptophan residue or a conservative substitution thereof; $X_4$ is a leucine residue or a conservative substitution thereof; $X_5$ is a threonine residue or a conservative substitution thereof; $X_6$ is an isoleucine residue or a conservative substitution thereof; $X_7$ is a tryptophan residue or a conservative substitution thereof and $X_8$ is a glycine residue or a conservative substitution thereof.

Given the above description a preferred peptide of the present invention is CGYWLTIWGC (SEQ ID NO: 35). In other preferred aspects, conservative amino acid substitutions of this peptide are contemplated. More particularly, one or more of the residues at $X_1$-$X_8$ of this peptide are subject to conservative substitution.

The term "conservative substitution" as used herein denotes the replacement of an amino acid residue by another, biologically similar residue with respect to hydrophobicity, hydrophilicity, cationic charge, anionic charge, shape, polarity and the like. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted or modified amino acid in place of an unsubstituted parent amino acid provided that antibodies raised to the substituted polypeptide also immunoreact with the unsubstituted polypeptide. By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Exemplary conservative substitutions are set out in the Table A below:

TABLE A

| Conservative Substitutions I | |
|---|---|
| SIDE CHAIN CHARACTERISTIC | AMINO ACID |
| Aliphatic | |
| Non-polar | G A P |
| | I L V |
| Polar-uncharged | C S T M |
| | N Q |
| Polar-charged | D E |
| | K R |
| Aromatic | H F W Y |
| Other | N Q D E |

Alternatively, conservative amino acids can be grouped as described in Lehninger, [*Biochemistry*, Second Edition; Worth Publishers, Inc. NY:NY (1975), pp. 71-77] as set out in Table B, immediately below.

TABLE B

| Conservative Substitutions II | |
|---|---|
| SIDE CHAIN CHARACTERISTIC | AMINO ACID |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Any conservative variant of CGYWLTIWGC (SEQ ID NO: 35) is contemplated to be a useful peptide of the present invention as long as such a variant retains its property of being a competitive inhibitor of VEGF-C/D binding to VEGFR-3. Additionally it is contemplated that non-conservative variants of these peptides also may be designed that may prove to be more efficient inhibitors of VEGF-C/D binding to VEGFR-3 than the original CGYWLTIWGC (SEQ ID NO: 35) identified by the present invention.

In another context it is of note that a 20 μmolar concentration GST-CGYWLTIWGC (SEQ ID NO: 35) fusion protein was sufficient completely inhibit VEGF-C/D binding to VEGFR-3 expressed on BaF3 cells. This indicates a relatively strong competitive binding. The ability of GST to form multimers may have contributed to the increased binding affinity of this fusion protein to the VEGFR-3. As such, it is contemplated that dimerization of the peptides may improve the inhibitory potency. Taking advantage of this observation, reselection using a CGYWX3WXC (SEQ ID NO: 73) secondary library in which residues denoted by X are randomized may be used to produce peptides of greater potency.

The preferred peptides of the present invention also may be made stable and protease resistant by preparing cyclic peptides XGYWLTIWGX (SEQ ID NO: 34), wherein the cysteine residues are replaced by amino acids making a new bond. Such a library of backbone cyclic peptides may be prepared in *E. coli* using an intein-based expression system. Methods of screening these peptides for higher binding affinity are described elsewhere in the specification.

Other methods of constructing peptides which are resistant to proteolytic digestion are also possible, such as peptides including non-hydrolyzable peptide bonds, and peptides having end modifications such as an amide (e.g., $CONH_2$) at the C-terminus or a acetyl group at the N-terminus. It is contemplated that the peptides of the invention are modified such that their in vivo half life is increase, their physical stability is increased, rate of in vivo release and rate of in vivo clearance also may be affected.

Preferably, the inhibitory peptides of the present invention are non-hydrolyzable. To provide such peptides, one may select peptides from a library non-hydrolyzable peptides, such as peptides containing one or more D-amino acids or peptides containing one or more non-hydrolyzable peptide bonds linking amino acids. Alternatively, one can select peptides which are optimal for inhibiting VEGF-C binding to VEGFR-3 and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of the inhibitory peptides of the present invention with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include $-[CH_2NH]-$ reduced amide peptide bonds, $-[COCH_2]-$ ketomethylene peptide bonds, $-[CH(CN)NH]-$ (cyanomethylene)amino peptide bonds, $-[CH_2CH(OH)]-$ hydroxyethylene peptide bonds, $-[CH_2O]-$ peptide bonds, and $-[CH_2S]-$ thiomethylene peptide bonds (see e.g., U.S. Pat. No. 6,172,043).

Peptides useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (Int. J Pep. Protein Res. 36:392-399, 1990) and Rivera—Baeza et al. (Neuropeptides 30:327-333, 1996) are also known in the art.

Furthermore, nonpeptide analogs of peptides which provide a stabilized structure or lessened biodegradation, are also contemplated. Peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., *Regul. Pept.* 57:359-370 (1995). Peptide as used herein embraces all of the foregoing.

If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the - or C-terminus In particular, it is anticipated that the aforementioned peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a peptide inhibitor of VEGF-C binding to VEGFR-3, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345 and 4,277,437. Other labels that will be useful include but are not limited to radioactive labels, fluorescent labels and chemiluminescent labels. U.S. Patents concerning use of such labels include for example U.S. Pat. Nos. 3,817,837; 3,850,752; 3,939,350 and 3,996,345. Any of the peptides of the present invention may comprise one, two, or more of any of these labels.

The peptides of the invention will be used as therapeutic compositions either alone or in combination with other therapeutic agents. For such therapeutic uses small molecules are generally preferred because the reduced size renders such peptides more accessible for uptake by the target. It is contemplated that the preferred peptides of the present invention are from about 6, 7, 8, 9, or 10 amino acid residues in length to about 100 amino acid residues in length. Of course it is contemplated that longer or indeed shorter peptides also may prove useful. Thus, peptides of 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 and a 100 amino acids in length will be particularly useful. Such peptides may be present as individual peptides or may coalesce into dimers or multimers for greater efficacy.

B. Methods of Making Peptides

The peptides of the present invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984);Tam et al., *J. Am. Chem. Soc.,* 105:6442, (1983); Merrifield, *Science,* 232: 341-347, (1986); and Barany and Merrifield, *The Peptides*, Gross and Meienhofer, eds, Academic Press, New York, 1-284; Barany et al., *Int. J. Peptide Protein Res.,* 30, 705-739 (1987); and U.S. Pat. No. 5,424,398), each incorporated herein by reference.

Solid phase peptide synthesis methods use a copoly(styrene-divinylbenzene) containing 0.1-1.0 mMol amines/g polymer. These methods for peptide synthesis use butyloxycarbonyl (t-BOC) or 9-fluorenylmethyloxycarbonyl(FMOC) protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9) On completion of chemical synthesis, the peptides can be deprotected to remove the t- t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Other methods, such as selecting peptides from a phage display library, are available for improving upon peptide specifically described herein. Libraries can be prepared from sets of amino acids as described herein. Phage display can be particularly effective in identifying binding peptides useful according to the invention. Briefly, one prepares a phage library (using e.g. ml 13, fd, or lambda phage), displaying inserts from 4 to about 80 amino acid residues. The inserts may represent, for example, a completely degenerate or biased array. One then can select phage-bearing inserts which bind to the VEGFR-3 receptor. This process can be repeated through several cycles of reselection of phage that bind to the VEGFR-3 receptor. Repeated rounds lead to enrichment of phage bearing particular sequences. DNA sequence analysis can be conducted to identify the sequences of the expressed polypeptides. The minimal linear portion of the sequence that binds to the VEGFR-3 receptor can be determined. One can repeat the procedure using a biased library containing inserts containing part or all of the minimal linear portion plus one or more additional degenerate residues upstream or downstream thereof. These techniques may identify peptides of the invention with still greater binding affinity for VEGFR-3 than peptides already identified herein. Also, screening resultant peptide against a second target (e.g., VEGFR-2) may identify peptides with multiple receptor binding affinities.

Yeast two-hybrid screening methods also may be used to identify polypeptides that bind to the VEGFR-3 receptor. Thus, the VEGFR-3 receptor, or a fragment thereof, can be used to screen peptide libraries, including phage display libraries, to identify and select inhibitory peptides of the present invention.

Alternatively, a variety of expression vector/host systems may be utilized to contain and express the VEGF-C competitive inhibitory peptides. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the protein are described herein below.

For example, the VEGF-C competitive inhibitory peptide may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted VEGF-C competitive inhibitory peptide is purified from the yeast growth medium by, e.g., the methods used to purify the VEGF-C competitive inhibitory peptide from bacterial and mammalian cell supernatants.

Alternatively, the cDNA encoding the peptide may be cloned into the baculovirus expression vector pVL1393 (PharMingen, San Diego, Calif.). This vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Md.), and resuspended in PBS. SDS-PAGE analysis shows a single band and confirms the size of the protein, and Edman sequencing on a Porton 2090 Peptide Sequencer confirms its N-terminal sequence.

Alternatively, the peptide may be expressed in an insect system. Insect systems for protein expression are well known to those of skill in the art. In one such system, *Autographa californica nuclear polyhedrosis virus* (ACNPV) is used as a vector to express foreign genes in *Spodoptera frugiperda* cells or in *Trichoplusia* larvae. The peptide coding sequence is cloned into a nonessential region of the virus, such as the polyhedrin gene, and placed under control of the polyhedrin promoter. Successful insertion of the peptide will render the polyhedrin gene inactive and produce recombinant virus lacking coat protein coat. The recombinant viruses are then used to infect *S. frugiperda* cells or *Trichoplusia* larvae in which peptide is expressed (Smith et al., *J Virol* 46: 584, 1983; Engelhard EK et al., *Proc Nat Acad Sci* 91: 3224-7, 1994).

In another example, the DNA sequence encoding the peptide is amplified by PCR and cloned into an appropriate vector for example, pGEX-3X (Pharmacia, Piscataway. N.J.). The pGEX vector is designed to produce a fusion protein comprising glutathione-S-transferase (GST), encoded by the vector, and a protein encoded by a DNA fragment inserted into the vector's cioning site. The primers for the PCR may be generated to include for example, an appropriate cleavage site.

Where the fusion partner was used solely to facilitate expression or is otherwise not desirable as an attachment to the peptide of interest, the recombinant fusion protein may then be cleaved from the GST portion of the fusion protein. The pGEX-3X/VEGF-C competitive inhibitory peptide construct is transformed into *E. coli* XL-1 Blue cells (Stratagene, La Jolla Calif.), and individual transformants were isolated and grown. Plasmid DNA from individual transformants is purified and partially sequenced using an automated sequencer to confirm the presence of the desired VEGF-C competitive inhibitory peptide encoding nucleic acid insert in the proper orientation.

Particularly preferred peptide compositions of the present invention are those which are conjugated to any anti-tumor peptide such as a tumor necrosis factor (TNF). In a particularly preferred method, the TNF-peptides chimeras are generated as recombinant fusions with peptide-encoding sequences fused in frame to TNF (Novagen) encoding sequences. Peptide-TNF cDNA is cloned into pET-11b vector (Novagen) and the expression of TNF-peptides in BL21 *E. coli* is induced according to the pET11b manufacturer's instruction. Soluble TNF-peptides are purified from bacterial lysates by ammonium sulfate preparation, hydrophobic interaction chromatography on Phenyl-Sepharose 6 Fast Flow, ion exchange chromatography on DEAE-Sepharose Fast Flow and gel filtration chromatography on Sephacryl-S-300 HR.

It is contemplated that recombinant protein production also may be used to produce the VEGF-C competitive inhibitory peptide compositions. For example, induction of the GST/VEGF-C competitive inhibitory peptide is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate is cleared by sonication, and cell debris is pelleted by centrifugation for 10 minutes at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/VEGF-C competitive inhibitory peptide fusion protein is produced in bacteria as a soluble protein, it may be purified using the GST Purification Module (Pharmacia Biotech).

The fusion protein may be subjected to digestion to cleave the GST from the VEGF-C competitive inhibitory peptide of the invention. The digestion reaction (20-40 μg fusion protein, 20-30 units human thrombin (4000 U/mg (Sigma) in 0.5 ml PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of VEGF-C competitive inhibitory peptide may be confirmed by amino acid sequence analysis using an automated sequencer (Applied Biosystems Model 473A, Foster City, Calif.). Alternatively, the identity may be confirmed by performing HPLC and/or mass spectometry of the peptides.

Alternatively, the DNA sequence encoding the VEGF-C competitive inhibitory peptide may be cloned into a plasmid containing a desired promoter and, optionally, a leader sequence (see, e.g., Better et al., *Science,* 240:1041-43, 1988). The sequence of this construct may be confirmed by automated sequencing. The plasmid is then transformed into *E. coli* strain MC1061 using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the VEGF-C competitive inhibitory peptide and be cleaved during secretion.

The secreted recombinant protein is purified from the bacterial culture media by the method described herein below.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; also that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

C. Assays for Monitoring Effects of the Peptides

The many biological activities mediated through the VEGF-C/D binding to VEGFR-3 receptor family (including but not limited to affecting growth and migration of vascular endothelial cells and blood vessels; promoting growth of lymphatic endothelial cells and lymphatic vessels; increasing vascular permeability; and affecting myelopoiesis) support numerous in vitro and in vivo clinical utilities for novel peptides of the invention. As indicated herein throughout these peptides are capable of binding one of more members of the VEGF receptor family, and in particular VEGFR-3 in a manner that competitively inhibits the binding and activity of VEGF-C/D. As such the peptides of the invention will be effective in inhibiting VEGF-C/D mediated biological responses. The present section describes various methods of monitoring the effects of the peptides and for screening for those novel peptides that have VEGFR-3 binding and/or inhibitory capability.

I. Binding to Soluble VEGF Receptor-Fc Fusion Proteins.

The peptides of the present invention may be tested for the ability to bind soluble VEGF receptor-Fc fusion proteins. Binding of the peptides to VEGFR-3 or indeeed, VEGFR-1, or VEGFR-2, may be analyzed in this manner. Exemplary binding assays have been described in Achen et al., *Proc Natl Acad Sci USA* 95:548-53 (1998), incorporated by reference in its entirety. These assays will generally comprise admixing the receptor and ligand (e.g., VEGFR-3 and VEGF-C) and determining the receptor binding in the presence and absence of the peptides of the present invention. Those peptides that decrease the binding of the ligand to the receptor will be considered inhibitors in the context of the present invention.

It will be appreciated that binding assays can be performed with any form of VEGF receptors that retain the ability to bind their respective ligands, including but not limited to whole cells that naturally express a receptor or that have been recombinantly modified to express the receptor; truncated, solublized extracellular ligand binding domains of receptors; fusions comprising receptor extracellular domains fused to other proteins such as alkaline phosphatase (e.g., VEGFR-2-AP described in Cao et al., *J. Biol. Chem.* 271:3154-62 (1996); U.S. Pat. No. 5,776,755)) or immunoglobulin sequences; and fusions comprising receptor extracellular domains fused to tag sequences (e.g., a polyhistidine tag) useful for capturing the protein with an antibody or with a solid support; and receptor extracellular domains chemically attached to solid supports such as CNBr-activated Sepharose beads.

In exemplary assays, receptor binding may assayed using constructs comprising the extracellular domain of a VEGF receptor fused to immunoglobulin constant region chains. To this effect, the first three Ig domains of VEGFR-3 (encoded by nucleotides 20-1005 of GenBank Acc. No. X68203) may be fused to the Fc fragment from the Signal-pIgPlus vector (Ingenius/Novagen/R&D Systems). This construct (VEGFR-3-Fc) may be stably expressed in Drosophila Schneider 2 (S2) cells, and purified using Protein A sepharose. Purity was analyzed by silver staining of a PAGE gel and the functionality of the fusion protein was tested by its ability to bind $^{35}$S-labeled VEGF-C protein. The VEGFR-2-Fc receptor comprises the first 3 Ig domains of VEGFR-2 (encoded by nucleotides 64-972 of GenBank Acc. No. X61656) fused to the Fc fragment in the pIg vector. The VEGFR-1-Fc receptor similarly consists of the first three Ig domains of VEGFR-1 an can be fused to the Fc fragment of the pIg vector.

II. Receptor Inhibition Assays

The VEGF-C/D inhibitory peptides of the invention may be used for therapeutic applications where inhibition of one or more VEGF receptors is desired. For example, a candidate peptide can be added to stable cell lines expressing a particular VEGF receptor whose activation is necessary for cell survival. Survival of the cell line indicates that the candidate peptide is able to bind and activate that particular VEGF receptor. On the other hand, death of the cell line indicates that the candidate peptide fails to activate the receptor. Exemplary cell-survival assays have been described in International Patent Publication No. WO 98/07832 and in Achen et al., *Proc Natl Acad Sci USA* 95:548-553 (1998), incorporated herein by reference. This assay employs Ba/F3-VEGFR2-EpoR cells, which are Ba/F3 pre-B cells that have been transfected with a plasmid encoding a chimeric receptor consisting of the extracellular domain of VEGFR-2 and the cytoplasmic domain of the erythropoietin receptor (EpoR). For testing the peptides of the present invention, a similar cell line may be created from VEGFR-3.

These cells are routinely passaged in interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-3 extracellular domain of the chimeric receptor. For example, binding of VEGF-C to the VEGFR-3 extracellular domain causes the cells to survive and proliferate in the absence of IL-3. Addition of the peptides of the present invention to the VEGF-C containing media will result in a competition of the VEGFR-3 between the peptides and the VEGF-C. Cell death in the presence of the peptides will be indicative of the inhibitory activity of these peptides.

Candidate peptides can be tested for binding to the VEGFR-3 extracellular domain and subsequent inhibition of the chimeric receptor by assaying for the decrease in cell survival in the absence of IL-3 and presence of VEGF-C.

In exemplary assays, cells are cultured in the presence of IL-3 until required, then washed three times in phosphate buffered saline (PBS), resuspended in IL-3-free cell culture medium (Dulbecco's Modified Eagle's Medium (DMEM) supplemented with fetal calf serum (10%), L-glutamine (1%), geneticin (1 mg/ml), streptomycin (100 μg/ml) and penicillin (60 μg/ml)), and replated in 96-well culture plates (Nunc, Denmark) at a density of approximately 10000 cells/well. To assay for receptor activity in the absence of the peptides of the present invention, VEGF-C is added to culture wells at final concentrations of $10^{-10}$ to $10^{-5}$ M and incubated for 1 hour at 37° C. in 10% $CO_2$. For assaying the ability of the candidate peptides to inhibit activation of the VEGFR-3/EpoR receptor, recombinant VEGF-C is added along with the peptides of the present invention to wells at a concentration to produce near-maximal survival of the Ba/F3-VEGFR3-EpoR cells (typically 500 ng/ml). The cells are then grown in culture for 48 hours, after which time a solution of 3-(3,4-dimethylthiazol-2-yl)-2,5-diphenyltetrazolium bromide (MTT; 500 μg/ml) is added to the cultures, and incubated for another 30 minutes. MTT is converted to a blue formazan product by mitochondria, thus staining living cells blue. Surviving blue cells in experiments where inhibition (candidate peptide+VEGF-C) was assayed are counted under a microscope with inverted optics (100× magnification) and compared to cell survival in the positive control (VEGF-C alone) wells.

III. VEGFR-2 (KDR) and VEGFR-3 (Flt4) Autophosphorylation Assays

As an alternative indicator of activity, the ability of a peptide to alter autophosphorylation of a particular VEGF receptor can also be examined. A candidate peptide is added to cells expressing a particular VEGF receptor. The cells are then lysed and immuoprecipitated with anti-VEGF receptor antiserum and analyzed by Western blotting using anti-phosphotyrosine antibodies to determine phosphorylation of the VEGF receptor.

The peptides of the invention may be tested in cells expressing a VEGF receptor. For example, PAE-KDR and PAE-VEGFR3 (FLT4) cells (Pajusola et al., *Oncogene,* 9:3545-55 (1994); Waltenberger et al., *J. Biol. Chem.,* 269: 26988-26995 (1994); U.S. Pat. No. 5,776,755) are grown in Ham's F12 medium-10% fetal calf serum (FCS), or confluent NIH 3T3 cells expressing VEGFR-3 are grown in DMEM medium. The cells are starved overnight in DMEM medium or Ham's F12 supplemented with 0.2% bovine serum albumin (BSA), and then incubated for 5 minutes with VEGF-C alone or the peptides of the present invention in combination with VEGF-C.

After addition of the peptides, the cells are washed twice with ice-cold Tris-Buffered Saline (TBS) containing 100 mM sodium orthovanadate and lysed in RIPA buffer containing 1 mM phenylmethylsulfonyl fluoride (PMSF), 0.1 U/ml aprotinin and 1 mM sodium orthovanadate. The lysates are sonicated, clarified by centrifugation at 16,000×g for 20 minutes and incubated for 3-6 hours on ice with 3-5 μl of antisera specific for VEGFR-3 or VEGFR-2. Immunoprecipitates are bound to protein A-Sepharose, washed three times with RIPA buffer containing 1 mM PMSF. lmM sodium orthovanadate, washed twice with 10 mM Tris-HCl (pH 7.4), and subjected to SDS-PAGE using a 7% gel. Polypeptides are transferred to nitrocellulose by Western blotting and analyzed using PY20 phosphotyrosine-specific monoclonal antibodies (Transduction Laboratories) or receptor-specific antiserum and the ECL detection method (Amersham Corp.).

The ability of a candidate to affect the autophosphorylation (detected using the anti-phosphotyrosine antibodies) is scored as modulating the receptor. The level of alteration observed for various concentrations of peptide, relative to known concentrations of VEGF-A or VEGF-C, provide an indication of the potency of receptor modulation. Polypeptides that have been shown to bind the receptor, but are incapable of stimulating receptor phosphorylation, are scored as inhibitors. Inhibitory activity can be further assayed by mixing a known receptor agonist such as recombinant VEGF-A or VEGF-C with either media alone or with concentrated conditioned media, to determine if the concentrated conditioned media inhibits VEGF-A-mediated or VEGF-C-mediated receptor phosphorylation.

IV. Receptor Binding Affinities

The peptides of the present invention are competitive inhibitors of VEGF-C for VEFR-3 binding. To measure the relative binding affinities of selected peptides, an ELISA-type approach may be employed. For example, to examine binding affinity for VEGFR-3, serial dilutions of competing VEGFR-3-IgG fusion proteins and a subsaturating concentration of the candidate peptide tagged with the myc epitope is added to microtitre plates coated with VEGFR-3, and incubated until equilibrium is established. The plates are then washed to remove unbound proteins. Peptides that remain bound to the VEGFR-3 coated plates are detected using an anti-myc antibody conjugated to a readily detectable label e.g., horseradish peroxidase. Binding affinities ($EC_{50}$) can be calculated as the concentration of competing VEGFR-IgG fusion protein that results in half-maximal binding. These values can be compared with those obtained from analysis of VEGF-C to determine changes in binding affinity of one or more of the VEGFRs. Similarly, binding to VEGFR-2 is accomplished by using a VEGFR-2-IgG fusion protein, and binding to VEGFR-1 is determined using a VEGFR-1-IgG fusion protein.

V. Endothelial Cell Migration

VEGF-C stimulates endothelial cell migration in collagen gel. The peptides of the invention may be examined to determine if their inhibitor activity of VEGF-C mediated endothelial cell migration in collagen gel, thus providing another indicia of biological activity. Exemplary cell migration assays have been described in International Patent Publication No. WO 98/33917, incorporated herein by reference. Briefly, bovine capillary endothelial cells (BCE) are seeded on top of a collagen layer in tissue culture plates. VEGF-C is placed in wells made in collagen gel approximately 4 mm away from the location of the attached BCE cells. The number of BCE cells that have migrated from the original area of attachment in the collagen gel towards the wells containing the VEGF-C is then counted to assess VEGF-C induced cell migration. Performing these assays in the presence of the peptides of the present invention will further provide an indication of the VEGF-C inhibitory activity of these peptides.

BCE cells (Folkman et al., *Proc. Natl. Acad. Sci.* (*USA*), 76:5217-5221 (1979)) are cultured as described in Pertovaara et al., *J. Biol. Chem.,* 269:6271-74 (1994). Collagen gels are prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. Tissue culture plates (5 cm diameter) are coated with about 1 mm thick layer of the solution, which is allowed to polymerize at 37° C. BCE cells are seeded atop this layer.

For the migration assays, the cells are allowed to attach inside a plastic ring (1 cm diameter) placed on top of the first collagen layer. After 30 minutes, the ring is removed and unattached cells are rinsed away. A second layer of collagen and a layer of growth medium (5% newborn calf serum (NCS)), solidified by 0.75% low melting point agar (FMC BioProducts, Rockland, Me.), are added. A well (3 mm diameter) is punched through all the layers on both sides of the cell spot at a distance of 4 mm, and media containing a VEGF-C polypeptide or media containing VEGF-C in combination with a peptide of the present invention is pipetted daily into the wells. Photomicrographs of the cells migrating out from the spot edge are taken, e.g., after six days, through an Olympus CK 2 inverted microscope equipped with phase-contrast optics. The migrating cells are counted after nuclear staining with the fluorescent dye bisbenzimide (1 mg/ml, Hoechst 33258, Sigma).

The number of cells migrating at different distances from the original area of attachment towards wells containing the VEGF-C or VEGF-C in combination with the a peptide of the present invention, are determined 6 days after addition of the media. The number of cells migrating out from the original ring of attachment are counted in five adjacent 0.5 mm×0.5 mm squares using a microscope ocular lens grid and 10× magnification with a fluorescence microscope. Cells migrating further than 0.5 mm are counted in a similar way by moving the grid in 0.5 mm steps.

The ability of a peptide of the invention to inhibit to VEGF-C mediated migration of BCE cells in indicative of the potential receptor antagonist/VEGF-C inhibitory activity of the peptide. A decrease in the number of migrating cells in the presence VEGF-C in combination with a peptide of the invention versus a similar concentration of VEGF-C alone provides an indication of the potency of antagonist activity. It is contemplated that the peptides bind the receptors expressed on BCE cells, but are incapable of stimulating migration, and as such are scored as potential inhibitors.

VI. Effect of Vascular Permeability

VEGF-C also is capable of increasing the permeability of blood vessels. The peptides of the invention are assayed to determine how these inhibitory peptides affect this biological activity of VEGF-C. For example, vascular permeability assays according to Miles and Miles, *J. Physiol* 118:228-257 (1952), incorporated herein in its entirety, are used to analyze the peptides. Briefly, following intravenous injection of a vital dye, such as pontamine sky blue, animals such as guinea pigs are injected intradermally with a composition containing the candidate peptide being examined are first mixed with VEGF-C at varying ratios (e.g., 50:1, 10:1, 5:1, 2:1, 1:1, 1:2, 1:5, 1:10) and the mixtures are injected intradermally into the animals. For controls, media alone or media containing VEGF-A or VEGF-C is injected in the same manner. After a period of time, the accumulation of dye at the injection site on the skin is measured. Those peptides that decrease permeability will result in less accumulation of dye at the injection site as compared to induction of vascular permeability by VEGF-C alone. In this manner, the ability of the peptides of the invention to inhibit VEGF-A-mediated or VEGF-C-mediated vascular permeability is assayed.

VII. Endothelial Cell Proliferation

The effect of the peptides on the mitogenic activity of VEGF-C can be examined using endothelial cell proliferation assays such as that described in Breier et al., *Dev* 114:521-532 (1992), incorporated herein in its entirety. The peptides may be assayed for this effect using bovine aortic endothelial (BAE) cells by adding the peptides in combination with VEGF-C to the BAE cells. A similar set of assays is set up in which only VEGF-C alone is added. After three days, the cells are dissociated with trypsin and counted using a cytometer to determine any effects of the peptides on the proliferative activity of the BAE cells.

VIII. In vivo Assays

Experiments may be conducted in transgenic mice to analyze the specific effects of the peptides in cancer tissues. The physiological effects in vivo provide an indication of receptor activation/inhibition profile and an indication of the potential therapeutic action of a peptide. In one variation, the human K14 keratin promoter which is active in the basal cells of stratified squamous epithelia [Vassar et al., *Proc. Natl. Acad. Sci.* (*USA*), 86:1563-1567 (1989)], is used as the expression control element in the recombinant VEGF-C transgene. The vector containing the K14 keratin promoter is described in Vassar et al., *Genes Dev.,* 5:714-727 (1991) and Nelson et al., *J. Cell Biol.* 97:244-251 (1983). An exemplary mouse is described in Jeltsch et al., *Science,* 276: 1423 (1997).

A DNA fragment containing the K14 promoter, VEGF-C protein CDNA, and K14 polyadenylation signal is synthesized, isolated, and injected into fertilized oocytes of the FVB-NIH mouse strain. The injected zygotes are transplanted to oviducts of pseudopregnant C57BL/6×DBA/2J hybrid mice. The resulting founder mice are then analyzed for the presence of the transgene by polymerase chain reaction of tail DNA using appropriate primers or by Southern analysis.

These transgenic mice are then examined for evidence of angiogenesis or lymphangiogenesis in the skin, such as the lymphangiogenesis seen in transgenic mice that overexpress VEGF-C [see International Publication WO98/33917]. Histological examination of K14-VEGF-C transgenic mice showed that in comparison to the skin of wildtype littermates, the dorsal dermis was atrophic and connective tissue was replaced by large lacunae devoid of red cells, but lined with a thin endothelial layer. These distended vessel-like structures resembled those seen in human lymphangiomas. The number of skin adnexal organs and hair follicles were reduced. In the snout region, an increased number of vessels was also seen.

Examination of the vessels in the skin of the transgenic mice using antibodies that recognize proteins specific for either blood or lymphatic vessels can further verify the identity of these vessels. Collagen types IV, XVIII [Muragaki et al., *Proc. Natl. Acad. Sci. USA,* 92: 8763-8776 (1995)] and laminin are expressed in vascular endothelial cells while desmoplakins I and II (Progen) are expressed in lymphatic endothelial cells. See Schmelz et al., *Differentiation,* 57: 97-117 (1994).

Having created the above transgenic with various concentrations of the peptides of the present invention will provide indications of the in vivo therapeutic efficacy of the peptides.

Additionally, a human breast cancer cell line transfected with VEGF-C is already confirmed to have lymphangiogenesis and lymphatic metastasis when it is orthotopically transplanted in the nude mice (Skobe et al., Natur Med. In press, 2001) After transplantation of the tumor, different doses of peptides are injected systemically such as intraperitoneally or intraveously once a day. Mice are sacrificed after 12 weeks. Using this model, it is possible to check the tumor volume, the size of lymphatic area and the extent of lymph node metastasis.

A corneal assay is yet another assay for the evaluation of angiogenesis and lymphangiogenesis. Recently, the inventors confirmed that it is also useful for assessment of lymphangiogenesis. Pellet containing VEGF-A induces only angiogenesis in the mouse cornea. But, pellet containing VEGF-C (160 ng) induces both angiogenesis and lymphangiogenesis. After transplatation of such pellet into cornea, several doses of peptide may be administered systemically. At day 6 angiogenesis can be investigated by intavital microscopy. Mice are sacrificed after the investigation. Eyes are excised, fixed in 4% PFA, embedded in paraffin and sectioned at 8 um. Immunohistochemistry with anti-LYVE-1 (specific lymphatic marker) [Banelji et al., J. Cell Biol. 144:789-801 (1999)], anti-VEGFR3 and anti-PECAM-1 antibodies is performed to evaluate the presence of blood vessels and lymphatic vessels.

IX. Myelopoiesis Assays

Overexpression of VEGF-C in the skin of K14-VEGF-C transgenic mice correlates with a distinct alteration in leukocyte populations [see International Publication WO98/33917]. Notably, the measured populations of neutrophils were markedly increased in the transgenic mice. The effects of the peptides on VEGFC-mediated hematopoiesis can be analyzed using fluorescence-activated cell sorting analysis using antibodies that recognize proteins expressed on specific leukocyte cell populations. The effects of the peptides of the invention on these mice will be indicative of the in vivo therapeutic effects of these compounds.

X. Effects on Growth and Differentiation of Human CD34+ Progenitor Cells In vitro Addition of VEGF-C to cultures of cord blood CD34+ cells induces cell proliferation. Co-culture of GM-CSF, IL-3, GM-CSF+IL-3, or GM-CSF+SCF with VEGF-C leads to an enhancement of proportions of myeloid cells [see International Publication WO98/33917]. Peptides of the invention can also be examined for their ability to inhibit this induction of growth of CD34+ progenitor cells in vitro. Human CD34+ progenitor cells (HPC, $10\times10^3$) are isolated from bone marrow or cord blood mononuclear cells using the MACS CD34 Progenitor cell Isolation Kit (Miltenyi Biotec, Bergish Gladbach, Germany), according to the instructions of the manufacturer and cultured in RPMI 1640 medium supplemented with L-glutamine (2.5 mM), penicillin (125 IE/ml), streptomycin (125 μg/ml) and pooled 10% umbilical cord blood (CB) plasma at 37° C. in a humidified atmosphere in the presence of 5% $CO_2$ for seven days, in the presence of VEGF-C (and optionally in also in the presence of one or more of GM-CSF, IL-3, GM-CSF+IL-3, or GM-CSF+SCF) with or without the peptides of the present invention at concentrations ranging from 10 ng/ml to 1 μg/ml. After seven days, total cell number is evaluated in each culture. After seven days, the cultures were analyzed to determine the percentages of CD34+ cells and mean fluorescence intensity.

XI. Analysis of Peptides Using CAM Assays

The choroallantoic membrane (CAM) assay described in e.g., Oh et al., *Dev Biol* 188:96-109 (1997), incorporated herein in its entirety, is a commonly used method to examine the in vivo effects of angiogenic factors. Using this assay, VEGF-A and VEGF-C have been shown to induce specifically the development of blood vessels and lymphatic vessels respectively [Oh et al., *Dev Biol* 188:96-109 (1997)]. Thus, this method can be used to study both the antiangiogenic and anti-lymphangiogenic properties of the peptides of the present invention.

Briefly, on day 4 of development, a window is cut out into the eggshell of chick or quail eggs. The embryos are checked for normal development, the window in the eggshell is sealed with cellotape, and the eggs are incubated until day 13 of development. Approximately 3.3 μg of VEGF-C alone is dissolved in 5 μl of distilled water is added to Thermanox coverslips (Nunc, Naperville, Ill.), which have been cut into disks with diameters of approximately 5 mm, and air dried. A similar set of assays is set up in which varying concentrations of the peptides of the present invention are combined with the VEGF-C solution. Disks without added protein are used as controls. The dried disks are then applied on the chorioallantoic membrane (CAM) of the eggs. After 3 days, the disks are removed and fixed in 3% glutaraldehyde and 2% formaldehyde and rinsed in 0.12 M sodium cacodylate buffer. The fixed specimens are photographed and analyzed morphologically with a stereo microscope and embedded in Epon resin (Serva, Germany) for semi- (0.75 μm) and ultrathin (70 nm) sectioning. Both semi- and ultrathin sections are cut using an Ultracut S (Leika, Germany). Ultrathins sections are analyzed by an EM 10 (Zeiss, Germany). Specimens are then analyzed for evidence of growth of new capillaries and/or lymphatic vessels. The absence or decrease in such growth in the presence of the peptides of the present invention would indicate that the peptides being examined are capable of inhibiting angiogenesis.

D. Methods of Treating VEGF-C Related Disorders

The present invention also involves, in another embodiment, the treatment of pathologies characterized by ligand-mediated activity of VEGFR-3. There are numerous disorders that may thus benefit from an intervention using the peptides of the present invention including but not limited to cancer, chronic inflammatory diseases, rheumatoid arthritis, psoriasis, diabetic retinopathy, and the like. The peptides of the present invention will be useful against any disorder that is mediated through the binding of VEGFC to VEGFR-3. The peptides of the present invention will have a therapeutic anti-lymphangiogenic effect. Additionally, it is contemplated that these peptides also will have an anti-angiogenic effect in a number of pathological conditions. Such conditions include, for example, neovascularization associated with liver diseases, hypertension, post-trauma, neovascularization in chronic hepatitis and other liver infections, neovascularization due to heat or cold trauma, dysfunction related to excess of hormone, creation of hemangiomas and restenosis following angioplasty.

Thus, the types of cancer that may be treated, according to the present invention, is limited only by the involvement of VEGFC and/or VEGFR-3. Thus, it is contemplated that a wide variety of tumors may be treated using the peptides of the present invention including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree or localized to a specific area and inhibited from spread to disparate sites. It may be that the tumor growth is completely blocked, however, or that some tumor regression is achieved. Clinical terminology such as "remission" and "reduction of tumor" burden also are contemplated given their normal usage. In the context of the present invention, the therapeutic effect may result from an inhibition of angiogenesis and/or an inhibition of lymphangiogenesis.

I. Protein Therapy

The peptides of the present invention will be used for the therapeutic intervention of the disorders discussed herein above as well as any other disorders that are mediated through the ligand mediated activity of VEGFR-3. These therapies will be particularly useful as anti-lymphangiogenesis and/or anti-angiogenic treatements, however it is contemplated that the instant invention is not limited to these beneficial effects. By "mediated through" the present invention refers to any biological events that result from the ligand mediated activity of VEGFR-3, such as, for example, result from VEGFR-3 mediated growth or that result from an abberation in the expression or activity of VEGFR-3. As discussed above, the peptides may be produced by recombinant expression means or generated by an automated peptide synthesizer. Formulations would be selected based on the route of administration and purpose including, but not limited to, liposomal formulations and classic pharmaceutical preparations.

Administration of the compositions can be systemic or local and may comprise a single site injection of a therapeutically effective amount of the peptide composition of the present invention. Any route known to those of skill in the art for the administration of a therapeutic composition of the invention is contemplated including for example, intravenous, intramuscular, subcutaneous or a catheter for long term administration. Alternatively, it is contemplated that the therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a period basis, for example, daily, weekly or monthly.

In general, peroral dosage forms for the therapeutic delivery of peptides is ineffective because in order for such a formulation to the efficacious, the peptide must be protected from the enzymatic environment of the gastrointestinal tract. Additionally, the peptide must be formulated such that it is readily absorbed by the epithelial cell barrier in sufficient concentrations to effect a therapeutic outcome. The peptides of the present invention may be formulated with uptake or absorption enhancers to increase their efficacy. Such enhancer include for example, salicylate, glycocholate/linoleate, glycholate, aprotinin, bacitracin, SDS caprate and the like. For an additional discussion of oral formulations of peptides for therapeutic delivery, those of skill in the art are referred to Fix (*J. Pharm. Sci.,* 85(12) 1282-1285, 1996) and Oliyai and Stella (*Ann. Rev. Pharmacol. Toxicol.,* 32:521-544, 1993).

The amounts of peptides in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses.

II. Genetic Based Therapies

The peptides of the present invention also may be provided in the form of a nucleic acid. Specifically, the vasculature of the cancer cell or the cancer cell itself may be contacted with an expression construct capable of providing the peptides of the present invention to the vasculature of the cell in a manner to allow the inhibition of VEGFR-3 in that vasculature. However, it seems that it is more likely that the therapeutic aspects of the present invention may employ gene-based therapies in combination with the peptide therapies of the present invention as discussed herein below.

For these embodiments, an exemplary expression construct comprises a virus or engineered construct derived from a viral genome. The expression construct generally comprises a nucleic acid encoding the gene to be expressed and also additional regulatory regions that will effect the expression of the gene in the cell to which it is administered. Such regulatory regions include for example promoters, enhancers, polyadenylation signals and the like.

It is now widely recognized that DNA may be introduced into a cell using a variety of viral vectors. In such embodiments, expression constructs comprising viral vectors containing the genes of interest may be adenoviral (see for example, U.S. Pat. Nos. 5,824,544; 5,707,618; 5,693,509; 5,670,488; 5,585,362; each incorporated herein by reference), retroviral (see for example, U.S. Pat. Nos. 5,888,502; 5,830,725; 5,770,414; 5,686,278; 4,861,719 each incorporated herein by reference), adeno-associated viral (see for example, U.S. Pat. Nos. 5,474,935; 5,139,941; 5,622,856; 5,658,776; 5,773,289; 5,789,390; 5,834,441; 5,863,541; 5,851,521; 5,252,479 each incorporated herein by reference), an adenoviral-adenoassociated viral hybrid (see for example, U.S. Pat. No. 5,856,152 incorporated herein by reference) or a vaccinia viral or a herpesviral (see for example, U.S. Pat. Nos. 5,879,934; 5,849,571; 5,830,727; 5,661,033; 5,328,688 each incorporated herein by reference) vector.

In other embodiments, non-viral delivery is contemplated. These include calcium phosphate precipitation (Graham and Van Der Eb, *Virology,* 52:456-467, 1973; Chen and Okayama, *Mol. Cell Biol.,* 7:2745-2752, 1987; Rippe et al., *Mol. Cell Biol.,* 10:689-695, 1990) DEAE-dextran (Gopal, *Mol. Cell Biol.,* 5:1188-1190, 1985), electroporation (Tur-Kaspa et al., *Mol. Cell Biol.,* 6:716-718, 1986; Potter et al., *Proc. Nat. Acad. Sci. USA,* 81:7161-7165, 1984), direct microinjection (Harland and Weintraub, *J. Cell Biol.,* 101:1094-1099, 1985.), DNA-loaded liposomes (Nicolau and Sene, *Biochim. Biophys. Acta,* 721:185-190, 1982; Fraley et al., *Proc. Natl. Acad. Sci. USA,* 76:3348-3352, 1979; Felgner, *Sci Am.* 276 (6):102-6, 1997; Felgner, *Hum Gene Ther.* 7(15):1791-3, 1996), cell sonication (Fechheimer et al., *Proc. Natl. Acad. Sci. USA,* 84:8463-8467, 1987), gene bombardment using high velocity microprojectiles (Yang et al., *Proc. Natl. Acad. Sci USA,* 87:9568-9572, 1990), and receptor-mediated transfection (Wu and Wu, *J. Biol. Chem.,* 262:4429-4432, 1987; Wu and Wu, *Biochemistry,* 27:887-892, 1988; Wu and Wu, *Adv. Drug Delivery Rev.,* 12:159-167, 1993).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, *In: Liver diseases, targeted diagnosis and therapy using specific receptors and ligands*, Wu G, Wu C ed., New York: Marcel Dekker, pp. 87-104, 1991). The addition of DNA to cationic liposomes causes a topological transition from liposomes to optically birefringent liquid-crystalline condensed globules (Radler et al., *Science,* 275(5301):810-4, 1997). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., *Science,* 243:375-378, 1989). In other embodiments, the liposome may be complexed or employed in conjunction with nuclear nonhistone chromosomal proteins (HMG-1) (Kato et al., *J. Biol. Chem.,* 266:3361-3364, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987, supra) and transferrin (Wagner et al., *Proc. Nat'l. Acad Sci. USA,* 87(9):3410–3414, 1990). Recently, a synthetic neoglycoprotein, which recognizes the same receptor as ASOR, has been used as a gene delivery vehicle (Ferkol et al., *FASEB J.,* 7:1081-1091, 1993; Perales et al., *Proc. Natl. Acad. Sci., USA* 91:4086-4090, 1994) and epidermal growth factor (EGF) has also been used to deliver genes to squamous carcinoma cells (Myers, EPO 0273085).

In other embodiments, the delivery vehicle may comprise a ligand and a liposome. For example, Nicoiau et al. (*Methods Enzymol.,* 149:157-176, 1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky et al. (*Proc. Nat. Acad. Sci. USA,* 81:7529-7533, 1984) successfully injected polyomavirus DNA in the form of $CaPO_4$ precipitates into liver and spleen of adult and newborn mice demonstrating active viral replication and acute infection. Benvenisty and Neshif (*Proc. Nat. Acad. Sci. USA,* 83:9551-9555, 1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., *Nature,* 327:70-73, 1987). Several devices for accelerating small particles have been developed. One such device relies on a high voltage discharge to generate an electrical current, which in turn provides the motive force (Yang et al., *Proc. Natl. Acad. Sci USA,* 87:9568-9572, 1990). The microprojectiles used have consisted of biologically inert substances such as tungsten or gold beads.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector or protein. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient; hopefully, any tumor cells in the sample have been killed.

III. Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In the context of the present invention, it is possible that the antibody, antibodies, antibody conjugates or immune effector cells target the selected tumor for therapy and the peptides of the present invention that are combined with the immunotherapy target the vasculature of the tumor thereby having a combined therapeutic effect.

The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

IV. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). One embodiment of the present invention, it is contemplated that the peptides of the present invention may be administered in conjunction with chemo- or radiotherapeutic intervention, immunotherapy, or with other anti-angiogenic/anti-lymphangiogenic therapy.

To kill cells, inhibit cell growth, inhibit metastasis, inhibit angiogenesis or otherwise reverse or reduce the malignant phenotype of tumor cells, using the methods and compositions of the present invention, one would generally contact a "target" cell, a tumor or its vasculature with the therapeutic peptides of the present invention (either as a peptide composition or as an expression construct that will express the peptide) and at least one other agent. These compositions would be provided in a combined amount effective to kill or inhibit proliferation of the cancer by killing and/or inhibiting the proliferation of the cancer cells and/or the endothelia of blood and lymphatic vessels supplying and serving the cancer cells. This process may involve contacting the cells with the peptide or expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the peptide or expression construct and the other includes the second agent.

Alternatively, the therapeutic treatment employing the peptides of the present invention may precede or follow the other agent treatment by intervals ranging from minutes to weeks. In embodiments where the other agent and expression construct are administered separately, one would generally ensure that a significant period of time did not expire between the time of each delivery, such that the agent and the peptide-based therapeutic would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated. In specific embodiments, an anti-cancer therapy may be delivered which directly attacks the cancer cells in a manner to kill, inhibit or necrotize the cancer cell, in addition a therapeutic composition based on the peptides of the present invention also is administered to the individual in amount effective to have an antiangiogenic and/or anti-lymphangiogenic effect. The peptide compositions may be administered following the other anti-cancer agent, before the other anti-cancer agent or indeed at the same time as the other anti-cancer agent.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells and/or the endothelia of the tumor vessels with an agent in addition to the therapeutic agent comprising one or more peptide of the present invention. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or cisplatin. Kinase inhibitors also contemplated to be useful in combination therapies with the peptides of the present invention. The agent may be prepared and used as a combined therapeutic composition, or kit, by combining it with a VEGF-C/D inhibitor peptide of the invention, as described above.

Agents that directly cross-link nucleic acids, specifically DNA, are envisaged to facilitate DNA damage leading to a synergistic, antineoplastic combination with VEGF-C/D competitive inhibitor peptide -based therapy. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

By way of example the following is a list of chemotherapeutic agents and the cancers which have been shown to be managed by administration of such agents. Combinations of these chemotherapeutics with the peptides of the present invention may prove to be useful in amelioration of various neoplastic disorders. Examples of these compounds include adriamycin (also known as doxorubicin), VP-16 (also known as etoposide), and the like, daunorubicin (intercalates into DNA, blocks DNA-directed RNA polymerase and inhibits DNA synthesis); mitomycin (also known as mutamycin and/or mitomycin-C) is an antibiotic isolated from the broth of Streptomyces caespitosus which has been shown to have antitumor activity; Actinomycin D also may be a useful drug to employ in combination with the peptides of the present invention because tumors which fail to respond to systemic treatment sometimes respond to local perfusion with dactinomycin which also is known to potentiate radiotherapy. It also is used in combination with primary surgery, radiotherapy, and other drugs, particularly vincristine and cyclophosphamide and has been found to be effective against Ewing's tumor, Kaposi's sarcoma, and soft-tissue sarcomas, choriocarcinoma, metastatic testicular carcinomas, Hodgkin's disease and non-Hodgkin's lymphomas.

Bleomycin is a mixture of cytotoxic glycopeptide antibiotics isolated from a strain of Streptomyces verticillus, is effective in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Cisplatin has been widely used to treat cancers such as metastatic testicular or ovarian carcinoma, advanced bladder cancer, head or neck cancer, cervical cancer, lung cancer or other tumors and may be a useful combination with the peptides of the present invention. VP16 (etoposide) and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS). Tumor Necrosis Factor [TNF; Cachectin] glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. TNF can be quite toxic when used alone in effective doses, so that the optimal regimens probably will use it in lower doses in combination with other drugs. Its immunosuppressive actions are potentiated by γ-interferon, so that the combination potentially is dangerous. A hybrid of TNF and interferon-α also has been found to possess anti-cancer activity.

Taxol an antimitotic agent original isolated from the bark of the ash tree, Taxus brevifolia, and its derivative paclitaxol have proven useful against breats cancer and may be used in the combination therapies of the present invention. Beneficial responses to vincristine have been reported in patients with a variety of other neoplasms, particularly Wilms' tumor, neuroblastoma, brain tumors, rhabdomyosarcoma, and carcinomas of the breast, bladder, and the male and female reproductive systems. Vinblastine also is indicated as a useful therapeutic in the same cancers as vincristine. The most frequent clinical use of vinblastine is with bleomycin and cisplatin in the curative therapy of metastatic testicular tumors. It is also active in Kaposi's sarcoma, neuroblastoma, and Letterer-Siwe disease (histiocytosis X), as well as in carcinoma of the breast and choriocarcinoma in women.

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. Melphalan is the active L-isomer of the D-isomer, known as medphalan, which is less active against certain animal tumors, and the dose needed to produce effects on chromosomes is larger than that required with the L-isomer. Melphalan is available in form suitable for oral administration and has been used to treat multiple myeloma. Available evidence suggests that about one third to one half of the patients with multiple myeloma show a favorable response to oral administration of the drug. Melphalan has been used in the treatment of epithelial ovarian carcinoma.

Cyclophosphamide is stable in the gastrointestinal tract, tolerated well and effective by the oral and parental routes and does not cause local vesication, necrosis, phlebitis or even pain. Chlorambucil, a bifunctional alkylating agent of the nitrogen mustard type that has been found active against selected human neoplastic diseases. Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of EGFR-3 inhibitor peptide-based therapeutic to patients with VEGFR-3-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining VEGF-C/D competitive inhibitor peptide-based therapies with chemo- and radiotherapies, it also is contemplated that combination with gene therapies will be advantageous. For example, targeting of VEGF-C/D competitive inhibitor peptide -based therapies and p53 or p16 mutations at the same time may produce an improved anticancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fins, jun, trk, ret, gsp, hst, bcl and abl.

In addition to the anticancer therapeutics discussed above, it is contemplated that the peptides of the invention may be combined with other angiogenesis inhibitors. The peptides of the present invention are expected to have both anti-lymphangiogenic and anti-angiogenic properties. Many anti-angiogenic drugs also may have anti-lymphangiogenic properties. http://cancertrials.nci.nih.gov/news/angio is a website maintained by the National Institutes of Health which provides current information on the trials presently being conducted with anti-angiogenic agents. These agents include, for example, Marimastat (British Biotech, Annapolis Md.; indicated for non-small cell lung, small cell lung and breast cancers); AG3340 (Agouron, LaJolla, Calif.; for glioblastoma multiforme); COL-3 (Collagenex, Newtown Pa.; for brain tumors); Neovastat (Aeterna, Quebec, Canada; for kidney and non-small cell lung cancer) BMS-275291 (Bristol-Myers Squibb, Wallingford Conn.; for metastatic non-small cell ling cancer); Thalidomide (Celgen; for melanoma, head and neck cancer, ovarian, metastatic prostate, and Kaposi's sarcoma; recurrent or metastatic colorectal cancer (with adjuvants); gynecologic sarcomas, liver cancer; multiple myeloma; CLL, recurrent or progressive brain cancer, multiple myeloma, non-small cell lung, nonmetastatic prostate, refractory multiple myeloma, and renal cancer); Squalamine (Magainin Pharmaceuticals Plymouth Meeting, Pa.; non-small cell cancer and ovarian cancer); Endostatin (EntreMEd, Rockville, Md.; for solid tumors); SU5416 (Sugen, San Francisco, Calif.; recurrent head and neck, advanced solid tumors, stage IIIB or IV breast cancer; recurrent or progressive brain (pediatric); Ovarian, AML; glioma, advanced malignancies, advanced colorectal, von-Hippel Lindau disease, advanced soft tissue; prostate cancer, colorectal cancer, metastatic melanoma, multiple myeloma, malignant mesothelioma: metastatic renal, advanced or recurrent head and neck, metastatic colorectal cancer); SU6668 (Sugen San Francisco, Calif.; advanced tumors); interferon-α; Anti-VEGF antibody (NAtional Cancer Institute, Bethesda Md.; Genentech San Franscisco, Calif.; refractory solid tumors; metastatic renal cell cancer, in untreated advanced colorectal); EMD121974 (Merck KCgaA, Darmstadt, Germany; HIV related Kaposi's Sarcoma, progressive or recurrent Anaplastic Glioma ); Interleukin 12 (Genetics Institute, Cambridge, Mass.; Kaposi's sarcoma) and IM862 (Cytran, Kirkland, Wash.; ovarian cancer, untreated metastatic cancers of colon and rectal origin and Kaposi's sarcoma). The parenthetical information following the agents indicates the cancers against which the agents are being used in these trials. It is contemplated that any of these disorders may be treated with the peptides of the present invention either alone or in combination with the agents listed.

Additionally, as mentioned above, the peptides of the present invention may proves effective in alleviating the symptoms of chronic inflammatory diseases, rheumatoid arthritis, psoriasis and diabetic retinopathy. It is contemplated that the peptides of the instant invention may be combined with traditional anti-inflammatory and other agents that are used in the management of these disorders.

F. Methods for Identifying Receptors

An additional use for the peptides of the present invention is in tissue imaging to determine whether a particular tissue is expressing a VEGFR-3 receptor. The use of such diagnostic imaging is particularly suitable in obtaining an image of, for example, a tumor mass or the neovascularizarion near a tumor mass. Previously, those of skill in the art have employed FLT4/VEGFR-3 antibodies for imagining purposes as described for example in U.S. Pat. No. 6,107,046 (incorporated herein by reference). It is contemplated that the peptides of the present invention may be employed for imaging in a manner analogous to the antibody-based methods disclosed in U.S. Pat. No. 6,107,046.

The peptides of the present invention may be coupled either covalently or noncovalently to a suitable supramagnetic, paramagnetic, electron-dense, echogenic or radioactive agent to produce a targeted imaging agent. In such embodiments, the peptide imaging agent will localize to the receptor and the area of localization be imaged using the above referenced techniques.

Many appropriate imaging agents are known in the art, as are methods of attaching the labeling agents to the peptides of the invention (see, e.g., U.S. Pat. Nos. 4,965,392, 4,472,509, 5,201,236 and 5,037,630, incorporated herein by reference). The labeled peptides are administered to a subject in a pharmaceutically acceptable carrier, and allowed to accumulate at a target site having the VEGFR-3 receptor. This peptide imaging agent then serves as a contrast reagent for X-ray, magnetic resonance, sonographic or scintigraphic imaging of the target site. The peptides of the present invention are a convenient and important addition to the available arsenal of medical imaging tools for the diagnostic investigation of cancer and other VEGFR-3 related disorders.

Paramagnetic ions useful in the imaging agents of the present invention include for example chromium (III), manganese (II), iron (III), iron (II), cobalt (II), nickel (II) copper (II), neodymium (III), samarium (III), ytterbium(III), gadolinium (III), vanadium (II), terbium (III), dysprosium (III), holmium (III) and erbium (III). Ions useful for X-ray imaging include but are not limited to lantanum (II), gold(III), lead (II) and particularly bismuth (III). Radioisotopes for diagnostic applications include for example, $^{211}$astatine, $^{14}$carbon, $^{51}$chromium, $^{36}$chlorine, $^{57}$cobalt, $^{67}$copper, $^{152}$Eu, $^{67}$gallium, $^{3}$hydrogen, $^{123}$iodine, $^{125}$iodine, $^{111}$indium, $^{59}$iron, $^{32}$phosphorus, $^{186}$rhenium, $^{75}$selenium, $^{35}$sulphur, $^{99m}$technicium and $^{90}$yttrium.

The peptides of the present invention may be labeled according to techniques well knonw to those of skill in the are. For example, the peptides can be iodinated by contacting the peptide with sodium or potassium iodide and a chemical oxidizing agent such as sodium hypochlorite or an enzymatic oxidant such as lactoperoxidase. Peptides may be labeled with technetium-99m by ligand exchange, for example, by reducing pertechnate with stannous solution, chelating the reduced technetium onto a Sephadex column and applying the peptide to the column. These and other techniques for labeling proteins and peptides are well knonw to those of skill in the art.

G. Formulations and Routes for Administration to Patients

In order to prepare peptide-containing compositions for clinical use, it will be necessary to prepare the therapeutic peptides of the present invention as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells Buffers also will be employed when recombinant cells are introduced into a patient. Aqueous compositions of the present invention comprise an effective amount of the peptide or an expression vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as 5any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylarnine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, where polypeptides are being administered parenterally, the polypeptide compositions are generally injected in doses ranging from 1 μg/kg to 100 mg/kg body weight/day, preferably at doses ranging from 0.1 mg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size.

Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood clotting levels in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100-fold) due to the presence of infection defective particles.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm ammals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

EXAMPLE

The following example provides experimental protocols for the production of exemplary peptides of the present invention. Briefly, phage-display libraries of random peptides were used to isolate specific peptides that possessed VEGFR-3 binding capacity. Through iterative rounds of bio-panning a novel peptide CGYWLTIWGC (SEQ ID NO: 35), which competes with VEGF-C binding to VEGFR-3 expressed on BaF3 cells was identified. This peptide is an effective antagonist of VEGF-C binding. The methods and results are described in further detail below.

Phage Display Peptide Libraries

In vitro biopanning using phage display libraries of random peptides was used to isolate specific peptides of the present invention (Koivunen et al., *Methods Mol. Biol.* 129: 3-17, 1999; Koivunen et al., *Biotechnol.,* 18(8):768-74, 1999). The synthetic inserts were synthesized as single-stranded degenerate oligonucleotides. The sequence of the template was:

5'-CACTCGGCCGACGGGGCT(NNK)xGGGGC-CGCTGGGGCCGAA-3' (SEQ ID NO: 74)

where N indicates an equimolar mixture of all four nucleotides; K indicates an equimolar mixture of G and T, preventing the introduction all but one stop codon into the sequence. X represents the number of repeats. 20 μg of the oligonucleotides was converted into double stranded by annealing 40 μg of the primer 5'-TTCGGCCCCAGCGGCCCC-3' (SEQ ID NO: 75) in a volume of 100 μl at 65 ° C. and slowly cooling to room temperature. Primer extension was performed by incubating the annealed oligonucleotides with 29 units of Sequenase 2.0 DNA polymerase (Amersham) for 60 min at 37 ° C. in a reaction volume of 250 μl containing 10 mM deoxynucleotides and 5 mM dithiothreitol. The double-stranded oligonucleotides were purified using QIAquick nucleotide removal kit according to the instructions of the manufacturer (QIAGEN) and eluted from each QIAquick column by 50 μl washes with $H_2O$. The oligonucleotides were digested with Bgl for 2 h at 37° C., purified again as above, and ligated into the fUSE5 vector(Smoth et al., *Methods Enzymol.,* 217:228-257, 1993). The plasmids were transfected into *E.coli* MC1061 by 200 individual electroporations, yielding primary libraries with more than $10^9$ members.

Production of VEGFR3-Fc Fusion Protein

The expression plasmids encoding human VEGFR3-Fc were constructed by PCR-amplification of the first three Ig homology domain of the extracellular portion of VEGFR-3 (GenBank accession number XM 003852) with the primer pairs 5'-CCTGGGATCCCTGGTGAGTGGCTACTCCATGAC-3' (SEQ ID NO: 76) (BamHI site underlined)/5'-GATGAAGAGATCTTCATGCACAATGACCTCGG-3' (SEQ ID NO: 77) (BglII site underlined). The product was cloned into the BglII site pMT/BiP-V5-His C vector (Invitrogen) and the cDNA coding for the Fc tail of human IgG1 was cloned in frame with VEGFR3 Ig homology domains into the same vector. The expression plasmids were co-transfected with the pCO-Hygro section plasmid (Invtrogen) into Drosophila S2 cells and stable cell pools were selected with 150 μg/ml Hygromycin B (Calbiochem). The expression of the VEGFR3-Fc fusion proteins was induced with 500 μM $CuSO_4$ in serum-free DES medium (Invitrogen). After four days, the fusion protein was purified from the conditioned medium by protein A affinity chromatography (Amersham).

Selection of VEGFR-3 Binding Phages

VEGFR3-Fc fusionprotein (1 μg/ml) was coated on microtiter wells (96-well plate) overnight at 4° C. Wells were then saturated with 5% BSA. In the first panning, the libraries were incubated overnight at 4° C. in 50 mM TBS buffer (Tris-HCl/0.1M NaCl, pH 7.5) containing 1% BSA. After extensive washing, the bounded phages were eluted with a low pH buffer (0.1M glycine-HCl, 0.1%BSA, 0.05% phenol red, pH2.2)(Koivunen et al., *Methods Mol. Biol.* 129:3-17,1999; Koivunenet al, *Biotechnol.,* 18(8):768-74,1999; Smoth et al., *Methods Enzymol.,* 217:228-357, 1993). In subsequent pannings, the amplified phages using the K91kan *E. coli*.(Koivunen et al., *Methods Mol. Biol.* 129:3-17, 1999) were allowed to bind for 1 h at room temperature. Randomly selected clones from the fourth round of panning were amplified overnight and sequenced using ABIPRISM 310 Genetic Analyzer. The binding of each clone to VEGFR-3 was verified by an attachment assay, in which the cloned phage were incubated for 60 minutes in VEGFR3-Fc-coated or BSA-blocked microtiter wells. Thewells were washed ten times with TBS containing 0.5% Tween-20. The bound phages were titered by calculating the number of colonies.

Production of Peptide Fusions with GST

The production of fusion proteins of the peptides of the invention with GST used methods described by Rajotte et al., (. J Clin Invest. Jul. 15 1998; 102(2):430-7). Briefly, PCR amplification of the peptide-coding inserts was performed on phage ssDNA using the primers:

5'-AGGCTCGAGGATCCTCGGCCGACGGGGCT-3' (SEQ ID NO: 78) and

5'-AGGTCTAGAATTCGCCCCAGCGGCCCC-3' (SEQ ID NO: 79).

Annealing temperature for PCR was 53° C. The PCR products were purified with QIAGEN gel extraction kit and digested with BamHI and EcoRI. Digested fragments were inserted in frame into the same sites of pGEX-2T vector (Pharmacia). GST-fusion proteins were produced in *E. coli* and purified according to manufacturer's instructions (Pharmacia). The molecular weight and purity of GST-fusion proteins were examined by SDS-PAGE.

Bioassay for VEGFR-3 Stimulation

For the viability assay, the IL-3 dependent BaF3 cells expressing a VEGFR-3/EpoR chimera (Aschen et al, *Eur J Biochem.* 267(9):2505-15, 2000) were seeded in 96 well microtiter plates at 15000 cells/well in triplicates in the absence of IL-3 but supplied with the lOOng/ml VEGF-C and a range of concentrations of the selected peptides fused with GST. Cells were cultured for 48 h, during which time the cells incubated in cell culture medium alone had died. The viability of the cells was determined by the MTT reagent, which was added at a concentration of 0.5 mg/ml. After 2 h an equal volume of cell lysis solution was added (10%SDS/10 mM HCl) and allowed to incubate overnight at 37° C. The absorbance was measured at 540 nm.

Results

To identify potential peptides binding to VEGFR-3, we performed in vitro bio-panning using phage-displayed libraries of random peptides. The $CX_7C$ $CX_8C$ (SEQ ID NO: 80), $X_9$ (SEQ ID NO: 70) and $CX_3CX_3CX_3C$ (SEQ ID NO: 71) peptide libraries composed of $10^9$ independent clones were screened by binding to immobilized VEGFR3-Fc fusion protein. Pronounced enrichment in phage binding to VEGFR3-Fc in relation to BSA (control) was detected (10-fold in the second, 200-fold in the third and fourth round panning). In a control experiments phage recovered from the third and fourth rounds did not bind to the Fc portion as studied by human IgG (850 ug/ml) on microtiter wells. The clones selected and analyzed by sequencing are listed in Table 1 earlier in the specification.

The effects of the peptides fused to GST on the growth of BaF3-R3/EpoR were assessed using the MTT assay as described above and are depicted in FIG. 1. In this experiment, GST- CGYWLTIWGC (SEQ ID NO: 35) fusion protein was used for the inhibition of VEGF-C binding to VEGFR-3 expressed on BaF3 cells. In this experiment, a 20 uM concentration of the fusion protein sufficed to inhibit the binding completely as measured by the MTT cell death assay. This suggests a relatively strong binding.

To screen for peptides having higher binding affinity, it is possible to use the cell-binding assay with VEGFR-3 transfected PAE cells. The VEGFR-3 transfected PAE cells is an established cell line. For binding assay, cells are plated in 24 wells plate at $1\times10^5$/well to reach a confluency the following day. Cells are washed and blocked with Hank's buffered saline (HBS) containing 1%BSA for one hour before adding the mixture of 125I-VEGF-C with increasing concentrations of peptides. The plates are incubated at 4 C. for three hours and then washed two times with HBS/BSA buffer. The bound VEGF-C is determined by solubilizing the washed cells with 1N NaOH and counting the radioactivity in a gamma-counter. 125I-VEGF-C is made by the chloramine-T method.

What is claimed is:

1. An isolated peptide comprising the amino acid sequence set forth in any one of SEQ ID NOs: 35-66, wherein the peptide is 8 to 25 amino acids in length and binds to human Vascular Endothelial Growth Factor Receptor-3 (VEGFR-3).

2. The isolated peptide according to claim 1, wherein the peptide comprises amino- and carboxy-terminal cysteine residues.

3. The isolated peptide according to claim 1, comprising the amino acid sequence set forth in any one of SEQ ID NOs: 35-43 and 55-66.

4. The isolated peptide of claim 1, wherein said peptide comprises the sequence CGYWLTIWGC (SEQ ID NO: 35).

5. The peptide of claim 3 or claim 4 wherein the peptide is 10-25 amino acids in length.

6. An isolated peptide comprising the amino acid sequence set forth in SEQ ID NO: 34, wherein the peptide is 10 to 25 amino acids in length and binds to human Vascular Endothelial Growth Factor Receptor-3 (VEGFR-3).

7. The isolated peptide according to claim 6, wherein the peptide comprises amino- and carboxy-terminal cysteine residues.

8. An isolated peptide comprising the amino acid sequence spanning amino acid residue 2 through amino acid residue 9 of any one of SEQ ID NOs: 35 and 55-58, wherein the peptide is 8 to 25 amino acids in length and binds to human Vascular Endothelial Growth Factor Receptor-3 (VEGFR-3).

9. The isolated peptide according to claim 8, wherein the peptide comprises amino- and carboxy-terminal cysteine residues.

10. The isolated peptide of claim 8 wherein the peptide is 10 to 20 amino acids in length.

11. The isolated peptide according to claim 1, 6, or 8, wherein said peptide further comprises an intramolecular bond between amino acid residues to form a cyclic peptide.

12. The isolated peptide according to claim 11, wherein the peptide comprises amino- and carboxy-terminal cysteines, and the intramolecular bond comprises a disulfide bond between the cysteines.

13. The isolated peptide according to claim 1, 6, or 8, wherein said peptide inhibits Vascular Endothelial Growth Factor C (VEGF-C) binding to the human VEGFR-3.

14. A peptide according to claim 1, 6 or 8, wherein the peptide is conjugated to a cytoxic agent or a label.

15. The peptide of claim 14, wherein the label is selected from the group consisting of a radionuclide, a dye, an enzyme, and an enzyme substrate.

16. The peptide according to claim 14, wherein the cytotoxic agent is a radioisotope.

17. The peptide according to claim 14, wherein the cytotoxic agent is an anti-neoplastic pro-drug.

18. A chimeric protein comprising a peptide according to claim 1, 6 or 8 attached to a tumor necrosis factor.

19. A chimeric protein comprising a peptide according to claim 1, 6 or 8 attached to an antibody or binding fragment thereof.

20. The isolated peptide of claim 1, 6, or 8, wherein said peptide further comprises a modification to increase the circulating in-vivo half-life of the peptide in a mammal wherein the modification is glycosylation, pegylation or inclusion of non-hydrolyzable bond.

21. A peptide dimer comprising first and second peptides according to claim 1, 6, or 8 wherein the peptide dimer binds to VEGFR-3.

22. The peptide dimer according to claim 21, wherein the first and second peptides comprise the same amino acid sequence.

23. A composition comprising an isolated peptide according to claim 1, 6, or 8 in a pharmaceutically acceptable carrier.

* * * * *

UNITED STATES PATENT AND TRADEMARK OFFICE

CERTIFICATE OF CORRECTION

PATENT NO. : 7,611,711 B2
APPLICATION NO. : 10/046922
DATED : November 3, 2009
INVENTOR(S) : Alitalo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 352 days.

Signed and Sealed this

Twelfth Day of October, 2010

David J. Kappos
*Director of the United States Patent and Trademark Office*